(12) United States Patent
Payne et al.

(10) Patent No.: US 7,285,406 B2
(45) Date of Patent: *Oct. 23, 2007

(54) **NUCLEIC ACID FRAGMENTS ENCODING NITRILE HYDRATASE AND AMIDASE ENZYMES FROM *COMAMONAS TESTOSTERONI* 5-MGAM-4D AND RECOMBINANT ORGANISMS EXPRESSING THOSE ENZYMES USEFUL FOR THE PRODUCTION OF AMIDES AND ACIDS**

(75) Inventors: Mark S. Payne, Wilmington, DE (US); Robert DiCosimo, Chadds Ford, PA (US); John E. Gavagan, Wilmington, DE (US); Robert D. Fallon, Elkton, MD (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/601,230

(22) Filed: Nov. 16, 2006

(65) Prior Publication Data

US 2007/0105197 A1 May 10, 2007

Related U.S. Application Data

(60) Division of application No. 10/977,893, filed on Oct. 29, 2004, now Pat. No. 7,153,663, which is a continuation-in-part of application No. 10/431,966, filed on May 8, 2003, now abandoned.

(51) Int. Cl.
*C12N 9/00* (2006.01)
*C12N 9/80* (2006.01)
*C12N 9/06* (2006.01)
*C12N 15/74* (2006.01)
*C12N 15/00* (2006.01)
*C07H 21/04* (2006.01)

(52) U.S. Cl. ............ 435/183; 435/69.2; 435/228; 435/191; 435/320; 435/471; 435/252.33; 435/252.34; 435/252.5; 435/252.35; 435/252.23; 435/255.2; 435/256.1; 435/256.3; 435/255.6; 435/254.4; 435/253.5; 435/252.6; 435/183

(58) Field of Classification Search ............ 435/183, 435/69.2, 228, 191, 320, 471, 252.33, 252.34, 435/252.5, 252.35, 254.23, 255.2, 256.1, 435/256.3, 255.6, 254.4, 253.5, 253.6; 536/23.2
See application file for complete search history.

(56) References Cited

U.S. PATENT DOCUMENTS 5,811,286 A 9/1998 Fallon et al.
6,670,158 B2 12/2003 DiCosimo et al.

FOREIGN PATENT DOCUMENTS

WO 95/04828 2/1995

OTHER PUBLICATIONS

Ludmila Martinkova et al., Nitrile-and Amide-converting Microbial Enzymes:Stereo-,Regio-and Chemoselectivity; Biocatalysis and Biotransformation, 20(2):73-93 (2002).
Don Cowen et al., Extremophiles, 2:207-216 (1998), Biochemistry and biotechnology of mesophllic and thermophilic nitrile metabolizing enzymes.
Makoto Nishiyama et al, Cloning and Characterization of Genes Responsible for Metabolism of Nitrile Compunds from *Pseudomonas chloroaphis* B23; J. Bacteriology, vol. 173 No. 8 :2465-2472 (1991).
Michihiko Kobayashi et al., Cloning, Amidase coupled with low-molecular-mass nitrile hydratase genes from *Rhodococcus rhodochrous* J1; Eur. J. Biochem., 217:327-336, 1993.
Jean-Francois Mayaux et al., Purification, Cloning, and Primary Sructure of an Enantiomer-Selective Amidase from Brevibacterium sp. Strain R312: Structural Evidence for Genetic Coupling with Nitrile Hydratese; J. Bacteriol., 172(12):6764-6773 (1990).
Osamu Ikehata et al., Primary structure of nitrile hydratase deduced from the nucleotide sequence of a Rhodocoddus species and its expression in *Escherichia coli*;Eur. J. Biochem., 181:563-570 (1989).
Mark S. Payne et al., A Stereoselective Cobalt-Containing Nirtile Hydratase: Biochemsirty, 36:5447-5454 (1997).
Toru Nagasawa et al., The superiority of the third-generation catalyst, *Rhodococcus rhodochrous* J1 nitrile hydratase, for Industrial production of acrylamide; Appl. Microbiol. Biotechnol., 40:189-195 (1993).
Rugmini Padmakumar and Patrick Oriel, Bioconversion of Acrylonitrile to Acrylamide Using a Thermostable Nitrile Hydratase; Appl. Biochem. Biotechnol., 77-79:671-679 (1999).
N.A. Webster et al., Comparative characterisation of two Rhodococcus species as potential biocatalysts for ammonium acrylate production; Biotechnology Letters, 23:95-101 (2001).
S. Wu et al., Over-production of stereoselective nitrite hydratase from *Pseudomonas putida* 5B in *Escherichia coli* : activity requires a novel downstrean protein; Appl. Microbiol. Biotechnol., 48:704-708 (1997).
S. Azza et al., FEMS Microbiol., Lett., 122:129-136, (1994), Cloning of the wide spectrum amidase gene from Brevlbacterium sp. And *Escherichia coli* .
Michihiko Kobayashi et al., Biochimica et Biophysica Acta., 1129:23-33, 1991, Cloning, nucleotide sequence and expression in *Escherichia coli* of two cobalt-containing nitrile hydratase genes from *Rhodococcus rhodochrous* J1.
Shijun Wu et al., DNA Cell Biol., 17(10):915-920 (1998), Cloning and Nucleotide Sequence of Amidase Gene from *Pseudomonas putida*.

*Primary Examiner*—David J. Steadman
*Assistant Examiner*—Kagnew Gebreyesus

(57) ABSTRACT

The invention relates to the isolation, sequencing, and recombinant expression of genes encoding either a nitrile hydratase (NHase) or amidase (Am) from *Comamonas testosteroni* 5-MGAM-4D, where the NHase is useful for catalyzing the hydration of nitrites to the corresponding amides, and the amidase is useful for hydrolysis of amides to the corresponding carboxylic acids. Also provided are transformed host cells containing polynucleotides for expressing the nitrile hydratase or amidase enzymes from *Comamonas testosteroni* 5-MGAM-4D.

9 Claims, 1 Drawing Sheet

Figure 1:
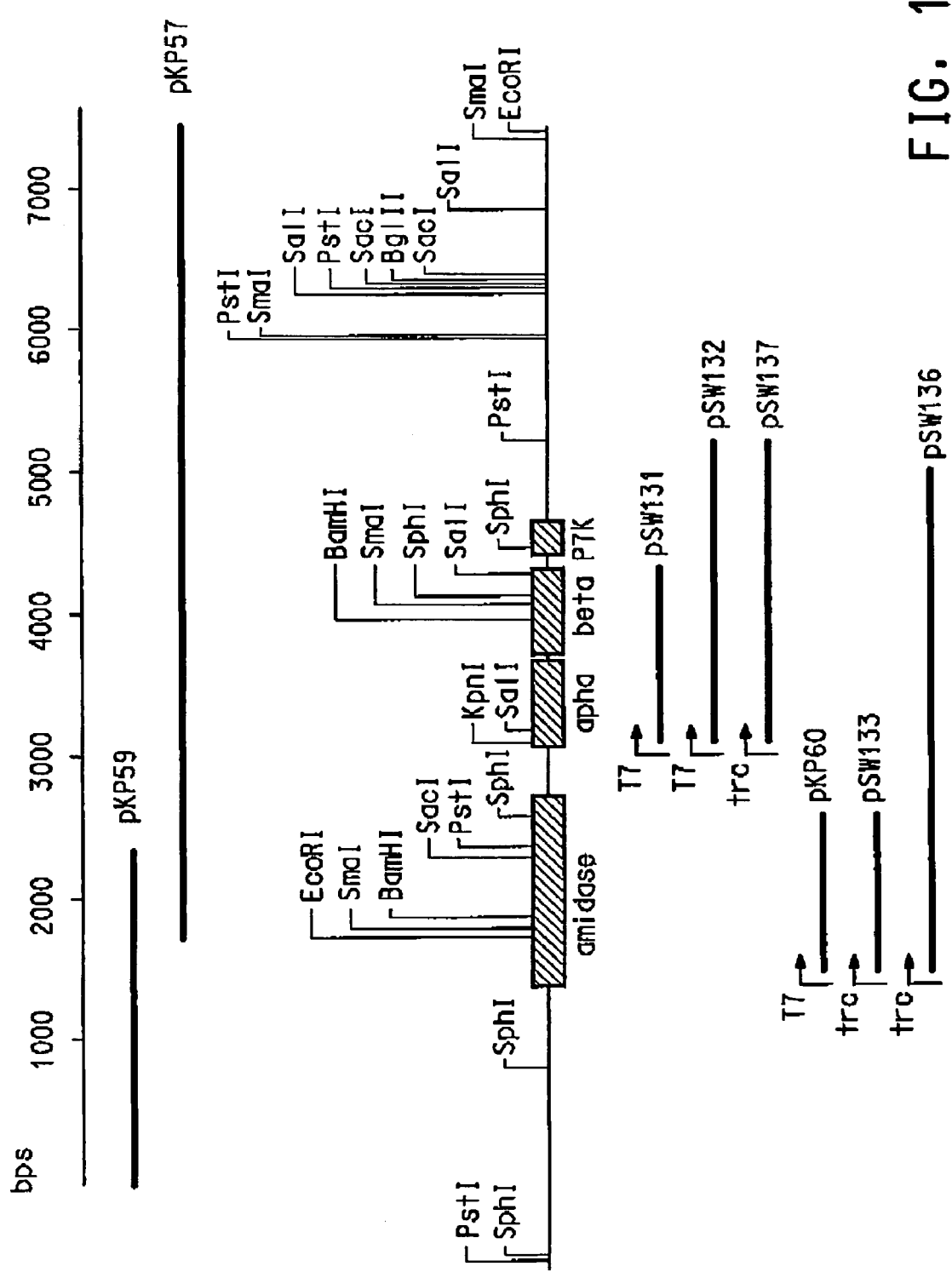

NUCLEIC ACID FRAGMENTS ENCODING NITRILE HYDRATASE AND AMIDASE ENZYMES FROM *COMAMONAS TESTOSTERONI* 5-MGAM-4D AND RECOMBINANT ORGANISMS EXPRESSING THOSE ENZYMES USEFUL FOR THE PRODUCTION OF AMIDES AND ACIDS

This application claims the benefit of U.S. application Ser. No. 10/977,893, filed Oct. 29, 2004 now U.S. Pat. No. 7,153,663, which is a continuation-in-part of U.S. application Ser. No. 10/431,966, filed May 8, 2003 now abandoned.

FIELD OF THE INVENTION

The present invention relates to the field of molecular biology and methods for the isolation and expression of foreign genes in recombinant microorganisms. More specifically, the invention relates to the isolation, sequencing, and recombinant expression of nucleic acid fragments (genes) encoding either a nitrile hydratase (NHase) or amidase (Am) from *Comamonas testosteroni* 5-MGAM-4D, where the NHase is useful for catalyzing the hydration of nitriles to the corresponding amides, and the amidase is likewise useful for hydrolysis of amides to the corresponding carboxylic acids.

BACKGROUND OF THE INVENTION

Nitrile hydratases catalyze the addition of one molecule of water to the nitrile, resulting in the formation of the corresponding amide according to Reaction 1:

$$R\text{—}CN + H_2O \rightarrow RCONH_2 \qquad \text{Reaction 1}$$

Similarly, methods for producing carboxylic acids are known and use microorganisms that produce an enzyme that possesses amidase (Am) activity. In general, amidases convert the amide product of Reaction 1 to the corresponding carboxylic acid plus ammonia according to Reaction 2:

$$RCONH_2 \rightarrow RCOOH + NH_3 \qquad \text{Reaction 2}$$

A wide variety of bacterial genera are known to possess a diverse spectrum of nitrile hydratase and amidase activities, including *Rhodococcus, Pseudomonas, Alcaligenes, Arthrobacter, Bacillus, Bacteridium, Brevibacterium, Corynebacterium*, and *Micrococcus* (Martinkova and Kren, *Biocatalysis and Biotransformation*, 20:73–93 (2002); Cowan et al., *Extremophiles*, 2:207–216 (1998)). For example, nitrile hydratase enzymes have been isolated from *Pseudomonas chlororaphis* B23 (Nishiyama et al., *J. Bacteriol.*, 173:2465–2472 (1991)), *Rhodococcus rhodochrous* J1 (Kobayashi et al., *Biochem. Biophys. Acta*, 1129:23–33 (1991)), *Brevibacterium* sp. 312 (Mayaux et al., *J. Bacteriol.*, 172:6764–6773 (1990)), *Rhodococcus* sp. N-774 (Ikehata et al., *Eur. J. Biochem.*, 181:563–570 (1989)), and *Pseudomonas putida* 5B NRRL-18668 (Payne et al., *Biochemistry*, 36:5447–5454 (1997)).

Wild-type microorganisms known to possess nitrile hydratase activity have been used to convert nitriles to the corresponding amides. Nagasawa et al. (*Appl. Microbiol. Biotechnol.*, 40:189–195 (1993)) have compared three microbial nitrile hydratase catalysts which have been used for commercial production of acrylamide from acrylonitrile; the nitrile hydratase activities of *Brevibacterium* R312 and *Pseudomonas chlororaphis* B23 were not stable above 10° C., compared to the nitrile hydratase activity of *Rhodococcus rhodochrous* J1. Cowan et al. (supra) reported that many mesophilic nitrile hydratases are remarkably unstable, having very short enzyme activity half-lives in the growth temperature range of 20–35° C. In addition to temperature instability, microbial catalysts containing a nitrile hydratase can be susceptible to inactivation by high concentrations of certain substrates such as acrylonitrile. In commercial use, the concentration of acrylonitrile was maintained at 1.5–2 wt % when using *Brevibacterium* R312 and *P. chlororaphis* B23 catalysts, while a concentration of up to 7 wt % was used with *R. rhodochrous* J1 (Nagasawa et al., supra). Similarly, Padmakumar and Oriel (*Appl. Biochem. Biotechnol.*, 77–79:671–679 (1999)) reported that *Bacillus* sp. BR449 expresses a thermostable nitrile hydratase, but when used for hydration of acrylonitrile to acrylamide, inactivation of the enzyme occurred at concentration of acrylonitrile of only 2 wt %, making this catalyst unsuitable for commercial applications. Webster et al. (*Biotechnology Letters*, 23:95–101 (2001)) compare two *Rhodococcus* isolates as catalysts for ammonium acrylate production (one with only a nitrilase activity, and one with only a combination of nitrile hydratase and amidase activities), and concluded that the catalyst having a combination of nitrile hydratase and amidase activities was less preferred due to (a) difficulty in inducing the two enzymes in the required ratio, (b) the susceptibility of the two enzymes (nitrile hydratase and amidase) to deactivation by acrylonitrile, and (c) inhibition of the two enzymes by the respective products.

The hydration of aromatic and heteroaromatic nitriles to the corresponding amides has been reported using the nitrile hydratase activity of *Rhodococcus rhodochrous* AJ270 (A. Meth-Cohn and M. Wang, *J. Chem Soc., Perkin Trans.* 1, (8):1099–1104 (1997)), where significant subsequent conversion of the amide to the corresponding acid by amidase was also observed. The nitrile hydratase activity of *Rhodococcus rhodochrous* J1 was used to convert a variety of aromatic and heteroaromatic nitriles to the corresponding amides with 100% molar conversion (J. Mauger et al., *Tetrahedron*, 45:1347–1354 (1989); J. Mauger et al., *J. Biotechnol.*, 8:87–96 (1988)); an inhibitory affect of certain nitriles on the nitrile hydratase was overcome by maintaining a low concentration of the nitrile over the course of the reaction. U.S. 20040142447 describes the use of several *Rhodococcus* strains for the conversion of 3-cyanopyridine to nicotinamide, where the *Rhodococcus* strains were relatively stable and had a relatively low Km value for 3-cyanopyridine when compared to previously-reported microbial cell catalysts.

In addition to the use of wild-type organisms, recombinant organisms containing heterologous genes for the expression of nitrile hydratase are also known for the conversion of nitrites. For example, Cerebelaud et al. (WO 9504828) teach the isolation and expression in *E. coli* of nitrile hydratase genes isolated from *C. testosteroni*. The transformed hosts effectively convert nitrites to amides, including substrates which consist of one nitrile and one carboxylate group. Endo et al. disclose the production of an *E. coli* transformant which expresses the nitrile hydratase of *Rhodococcus* N-771 (U.S. Pat. No. 6,316,242 B1). Similarly, Beppu et al., (EP 5024576) disclose plasmids carrying both nitrile hydratase and amidase genes from *Rhodococcus* capable of transforming *E. coli* where the transformed host is then able to use isobutyronitrile and isobutyramide as enzymatic substrates. A stereoselective nitrile hydratase from *Pseudomonas putida* 5B has been overproduced in *E. coli* (Wu et al., *Appl. Microbiol. Biotechnol.*, 48:704–708 (1997); U.S. Pat. No. 5,811,286).

Genes encoding enzymes having amidase activity have also been cloned, sequenced, and expressed in recombinant organisms. For example, Azza et al., (*FEMS Microbiol. Lett.*, 122:129 (1994)) disclose the cloning and over-expression in *E. coli* of an amidase gene from *Brevibacterium* sp. R312 under the control of the native promoter. Similarly, Kobayashi et al., (*Eur. J. Biochem.*, 217:327 (1993)) teach the cloning of both a nitrile hydratase and amidase gene from *R. rhodococcus* J1 and their co-expression in *E. coli*. Wu et al. (*DNA Cell Biol.*, 17:915–920 (1998); U.S. Pat. No. 6,251,650) report the cloning and overexpressing of a gene for amidase from *Pseudomonas putida* 5B in *E. coli*.

Applicants have previously isolated *Comamonas testosteroni* 5-MGAM-4D (ATCC 55744; U.S. Pat. No. 5,858,736 and U.S. Pat. No. 5,922,589). *Comamonas testosteroni* 5-MGAM-4D has been shown to contain thermally-stable, regiospecific nitrile hydratase (EC 4.2.1.84) and amidase (EC 3.5.1.4) activities useful in the conversion of a variety of nitriles to their corresponding amides and carboxylic acids. Methods illustrating the utility of the *Comamonas testosteroni* 5-MGAM-4D nitrile hydratase and amidase activities have been described previously by the Applicants. These uses include regio-selective preparation of lactams from aliphatic α,ω-dinitriles (U.S. Pat. No. 5,858,736), bioconversion of 3-hydroxynitriles to 3-hydroxyacids (US 2002/0039770 A1), and bioconversion of methacrylonitrile and acrylonitrile to their corresponding carboxylic acids (U.S. Ser. No. 10/067,652), hereby incorporated by reference. However, the isolation and recombinant expression of the nucleic acid fragments encoding the nitrile hydratase and amidase from *Comamonas testosteroni* 5-MGAM-4D has been elusive.

The problem to be solved is to provide the genes and encoding for the thermally-stable, regio-selective nitrile hydratase and amidase enzymes from *Comamonas testosteroni* 5-MGAM-4D and to provide transformants expressing these catalysts.

Additionally, the development of industrial processes which employ microbial catalysts having nitrile hydratase/amidase activities to efficiently manufacture amides or carboxylic acids has proved difficult. Many methods using enzyme catalysts to prepare these products from the corresponding nitriles do not produce and accumulate the product at a sufficiently high concentration to meet commercial needs, or are subject to enzyme inactivation (requiring a low concentration of nitrile over the course of the reaction) or product inhibition during the course of the reaction.

The additional problem to be solved continues to be the lack of facile microbial catalysts to convert nitrites to the corresponding amides or acids in a process characterized by high yield, high concentration, and high selectivity, and with the added advantages of low temperature and energy requirements and low waste production when compared to known chemical methods of nitrile hydrolysis. *Comamonas testosteroni* 5-MGAM-4D expresses a thermally-stable, regio-selective nitrile hydratase as well as a thermally-stable amidase. An enzyme catalyst having only the nitrile hydratase activity of *Comamonas testosteroni* 5-MGAM-4D would be highly useful in applications where only the amide product from nitrile hydration is desired.

SUMMARY OF THE INVENTION

The Applicants have isolated and sequenced the genes necessary to express thermally-stable, regio-selective nitrile hydratase and amidase from *Comamonas testosteroni* 5-MGAM-4D. The corresponding amino acid sequences for each enzyme are also disclosed. The invention also encompasses 1) an isolated polynucleotide encoding a polypeptide having at least 98% identity to a polypeptide alpha-subunit of the nitrile hydratase enzyme from *Comamonas testosteroni* 5-MGAM-4D as represented by SEQ ID No:4; 2) an isolated polynucleotide encoding a polypeptide having at least 95% identity to a polypeptide beta-subunit of the nitrile hydratase enzyme from *Comamonas testosteroni* 5-MGAM-4D as represented by SEQ ID No:6; and 3) an isolated polynucleotide encoding a polypeptide having amidase activity and having at least 95% identity to the polypeptide from *Comamonas testosteroni* 5-MGAM-4D as represented by SEQ ID No:17.

The invention further provides a region of the *Comamonas testosteroni* 5-MGAM-4D genome encompassed within a 0.9 kb fragment (SEQ ID NO:9) which encodes a polypeptide (designated "PK7"; and represented by SEQ ID NO:14) that is necessary for optimum activity of the nitrile hydratase enzyme.

Transformants are provided which express either the nitrile hydratase or amidase enzymes separately or which co-express both enzymes. Also provided are methods to produce the nitrile hydratase and amidase catalysts in a recombinant host. The present invention further provides recombinant hosts, transformed with the polynucleotides encoding the amidase and/or the nitrile hydratase in combination with the PK7 accessory protein.

A particular embodiment of the invention is *Escherichia coli* transformed with the nucleic acid sequence represented by SEQ ID NO:11.

The Applicants also provide methods for converting a variety of aliphatic nitriles, aromatic nitrites, heterocyclic aromatic nitrites, unsaturated nitrites, aliphatic dinitriles, and 2-, 3-, or 4-hydroxynitriles to the corresponding amides using a transformed host cell expressing the nitrile hydratase from *Comamonas testosteroni* 5-MGAM-4D. *Comamonas testosteroni* 5-MGAM-4D expresses a thermally-stable, regioselective nitrile hydratase as well as a thermally-stable amidase. The present application describes the preparation of microbial transformants that have only the nitrile hydratase activity of *Comamonas testosteroni* 5-MGAM-4D for use in applications where the production of only the amide product from nitrile hydration would be desirable.

BRIEF DESCRIPTION OF THE DRAWINGS SEQUENCE DESCRIPTIONS, AND BIOLOGICAL DEPOSITS

The invention can be more fully understood from the FIGURE, the Sequence Listing, the Biological Deposits, and the detailed description that together form this application.

FIG. 1 shows the nucleic acid fragments inserted in several plasmids created for recombinant expression of genes cloned from *Comamonas testosteroni* 5-MGAM-4D (ATCC 55744).

The following sequences comply with 37 C.F.R. 1.821–1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 is the nucleic acid sequence encoding the α-subunit of a nitrile hydratase from *Pseudomonas putida* 5B (NRRL-18668) used to probe genomic DNA fragments from *Comamonas testosteroni* 5-MGAM-4D (ATCC 55744).

SEQ ID NO:2 is the nucleic acid sequence encoding the β-subunit of a nitrile hydratase from *Pseudomonas putida* 5B (NRRL-18668) used to probe genomic DNA fragments from *Comamonas testosteroni* 5-MGAM-4D (ATCC 55744).

SEQ ID NO:3 is the nucleic acid sequence encoding the α-subunit of a nitrile hydratase from *Comamonas testosteroni* 5-MGAM-4D.

SEQ ID NO:4 is the deduced amino acid sequence for the α-subunit of a nitrile hydratase from *Comamonas testosteroni* 5-MGAM-4D.

SEQ ID NO:5 is the nucleic acid sequence encoding the β-subunit of a nitrile hydratase from *Comamonas testosteroni* 5-MGAM-4D.

SEQ ID NO:6 is the deduced amino acid sequence for the β-subunit of a nitrile hydratase from *Comamonas testosteroni* 5-MGAM-4D.

SEQ ID NO:7 is the nucleic acid sequence encoding the α- and β-subunits of the nitrile hydratase from *Comamonas testosteroni* 5-MGAM-4D used in the creation of pSW131.

SEQ ID NO:8 is the first of two primers ("Primer 1") useful for amplifying a nucleic acid fragment (SEQ ID NO:7) for creation of plasmid pSW131 and for amplifying a nucleic acid fragment (SEQ ID NO:11) for creation of pSW137.

SEQ ID NO:9 is the second of two primers ("Primer 2") useful for amplifying a nucleic acid fragment (SEQ ID NO:7) for creation of plasmid pSW131.

SEQ ID NO:10 is the nucleic acid sequence of a 0.9 kb nucleic acid fragment from *Comamonas testosteroni* 5-MGAM-4D containing a small open reading frame (ORF) which encodes an accessory protein (denoted as "P7K") useful in the expression of active nitrile hydratase.

SEQ ID NO:11 is the nucleic acid sequence encoding the α- and β-subunits of the nitrile hydratase plus 0.9 kb of downstream DNA (SEQ ID NO. 10) encoding the accessory protein P7K from *Comamonas testosteroni* 5-MGAM-4D used in the creation of pSW132 and pSW137.

SEQ ID NO:12 is the second of two primers ("Primer 3") useful for amplifying a nucleic acid fragment (SEQ ID NO:11) for creation of pSW137 and for amplifying a nucleic acid fragment (SEQ ID NO:23) for creation of pSW136.

SEQ ID NO:13 is the nucleic acid sequence encoding the accessory protein P7K, and found within the 0.9 kb downstream DNA sequence (SEQ ID NO:10) from *Comamonas testosteroni* 5-MGAM-4D.

SEQ ID NO:14 is the deduced amino acid sequence for the accessory protein P7K useful in the recombinant expression of *Comamonas testosteroni* 5-MGAM-4D nitrile hydratase.

SEQ ID NO:15 is the nucleic acid sequence of a nucleic acid fragment comprising the first 0.6 kb of the pKP57 insert useful as a probe to identify an amidase from *Comamonas testosteroni* 5-MGAM-4D.

SEQ ID NO:16 is the nucleic acid sequence encoding an amidase from *Comamonas testosteroni* 5-MGAM-4D.

SEQ ID NO:17 is the deduced amino acid sequence of an amidase from *Comamonas testosteroni* 5-MGAM-4D.

SEQ ID NO:18 is the nucleic acid sequence of 7.4 kb nucleic acid fragment comprising the complete coding sequences for an amidase and a nitrile hydratase and the P7K accessory protein from *Comamonas testosteroni* 5-MGAM-4D.

SEQ ID NO:19 is the first of two primers ("Primer 4") useful for amplifying a nucleic acid fragment encoding an amidase from *Comamonas testosteroni* 5-MGAM-4D for creation of plasmid pKP60. SEQ ID NO:20 is the second of two primers ("Primer 5") useful for amplifying a nucleic acid fragment encoding an amidase from *Comamonas testosteroni* 5-MGAM-4D for creation of plasmid pKP60.

SEQ ID NO:21 is the first of two primers ("Primer 6") useful for amplifying a nucleic acid fragment encoding an amidase from *Comamonas testosteroni* 5-MGAM-4D for creation of plasmid pSW133 and for amplifying a nucleic acid fragment (SEQ ID NO:23) for creation of pSW136.

SEQ ID NO:22 is the second of two primers ("Primer 7") useful for amplifying a nucleic acid fragment encoding an amidase from *Comamonas testosteroni* 5-MGAM-4D for creation of plasmid pSW133.

SEQ ID NO:23 is the nucleic acid fragment encoding an amidase, a nitrile hydratase (α- and β-subunits), and the accessory protein P7K from *Comamonas testosteroni* 5-MGAM-4D used in the creation of plasmid pSW136.

Applicants have made the following biological deposits under the terms of the Budapest Treaty on the International Recognition of the Deposit of Microorganisms for the Purposes of Patent Procedure:

| Depositor Identification Reference | Int'l. Depository Designation | Date of Deposit |
| --- | --- | --- |
| *Comamonas testosteroni* 5-MGAM-4D | ATCC 55744 | 8 Mar. 1996 |
| *Pseudomonas putida* 5B | NRRL 18668 | 6 Jul. 1990 |
| *Escherichia coli* SW132 | ATCC PTA-5073 | 21 Mar. 2003 |
| *Escherichia coli* SW137 | ATCC PTA-5074 | 21 Mar. 2003 |

As used herein, "ATCC" refers to the American Type Culture Collection International Depository Authority located at ATCC, 10801 University Blvd., Manassas, Va. 20110-2209, USA. The "International Depository Designation" is the accession number to the culture on deposit with ATCC.

As used herein, "NRRL" refers to the Northern Regional Research Laboratory, Agricultural Research Service Culture Collection International Depository Authority located at 11815 N. University Street, Peoria, Ill. 61604 U.S.A. The "NRRL No." is the accession number to cultures on deposit at the NRRL.

The listed deposits will be maintained in the indicated international depository for at least thirty (30) years and will be made available to the public upon the grant of a patent disclosing it. The availability of a deposit does not constitute a license to practice the subject invention in derogation of patent rights granted by government action.

DETAILED DESCRIPTION OF THE INVENTION

The present invention provides isolated polynucleotides and the nucleic acid sequences that encode three polypeptides (α- and β-subunits of a nitrile hydratase and an amidase) from *Comamonas testosteroni* 5-MGAM-4D (ATCC 55744) that act as catalysts. When coexpressed, the α- and β-subunits of the nitrile hydratase selectively hydrate nitriles into the corresponding amides, and the amidase hydrolyzes amides into the corresponding carboxylic acids. The invention also provides transformed microbial host cells expressing the polypeptides. The invention further provides a method for producing the polypeptide catalysts using the transformed microbes and a method for using the catalysts for converting nitriles to the corresponding amides and/or carboxylic acids, or for converting amides to the corresponding carboxylic acids.

Definitions:

In this disclosure, a number of terms and abbreviations are used. The following definitions apply unless specifically stated otherwise.

The terms "catalyst", "enzyme catalyst" or "microbial cell catalyst" refer to polypeptides (or proteins) having a nitrile hydratase activity, an amidase activity, or having a combination of nitrile hydratase and amidase activities. The catalyst may be in the form of an intact microbial cell, permeabilized microbial cell(s), one or more cell components of a microbial cell extract, partially purified enzyme(s), or purified enzyme(s).

As used herein, the term "comprising" means the presence of the stated features, integers, steps, or components as referred to in the claims, but that it does not preclude the presence or addition of one or more other features, integers, steps, components or groups thereof.

The term "thermally-stable" characterizes an enzyme that retains activity despite exposure to a given temperature.

The terms "*Comamonas testosteroni*" and "*C. testosteroni*" are used interchangeably and refer to *Comamonas testosteroni* 5-MGAM-4D (ATCC 55744).

The terms "*Psuedomonas putida* 5B" and "*P. putida* 5B" are used interchangeably and refer to *Psuedomonas putida* NRRL-18668.

The terms "*Escherichia coli* SW132" and "*E. coli* SW132" are used interchangeably and refer to an *E. coli* strain transformed with plasmid pSW132 and having ATCC accession number PTA-5073.

The term "pSW132" refers to a plasmid containing a DNA fragment encoding the *C. testosteroni* 5-MGAM-4D nitrile hydratase α- and β-subunits plus 0.9 kb of downstream DNA under the control of the T7 promoter. The 0.9 kb of downstream DNA encodes an accessory protein ("P7K") useful in recombinant expression of nitrile hydratase. *E. coli* strain SW132 harbors plasmid pSW132 and has ATCC accession number PTA-5073.

The terms "*Escherichia coli* SW137" and "*E. coli* SW137" are used interchangeably and refer to an *E. coli* strain transformed with plasmid pSW137 and having ATCC accession number PTA-5074.

The term "pSW137" refers to a plasmid containing a DNA fragment encoding the *C. testosteroni* 5-MGAM-4D nitrile hydratase α- and β-subunits plus 0.9 kb of downstream DNA under the control of the trc promoter. The 0.9 kb of downstream DNA encodes an accessory protein ("P7K") useful in recombinant expression of nitrile hydratase. *E. coli* strain SW137 harbors plasmid pSW137 and has ATCC accession number PTA-5074.

"Open reading frame" is abbreviated ORF.

"Polymerase chain reaction" is abbreviated PCR.

As used herein, an "isolated nucleic acid fragment" or "isolated polynucleotide" is a polymer of RNA or DNA that is single- or double-stranded, optionally containing synthetic, non-natural, or altered nucleotide bases. An isolated nucleic acid fragment in the form of a polymer of DNA may be comprised of one or more segments of cDNA, genomic DNA, or synthetic DNA.

The term "accessory nucleic acid" refers to the 0.9 kb sequence (SEQ ID NO:10), located downstream of the nitrile hydratase α (alpha) and β (beta) subunit genes, which contains an open reading frame (SEQ ID NO:13) encoding a polypeptide (SEQ ID NO:14) useful in increased recombinant expression of the nitrile hydratase.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, NY (1988); *Biocomputing: Informatics and Genome Projects* (Smith, D. W., ed.) Academic Press, NY (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences may be performed using the CLUSTAL method of alignment (Higgins and Sharp *CABIOS.* 5:151–153 (1989)) with the default parameters (GAP PENALTY=10, GAP LENGTH PENALTY=10). Default parameters typically used for pairwise alignments using the CLUSTAL method are KTUPLE 1, GAP PENALTY=3, WINDOW=5 and DIAGONALS SAVED=5.

"Codon degeneracy" refers to the nature in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the instant microbial polypeptides as set forth in SEQ ID NOs:4, 6, 14, and 17. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

"Transformation" refers to the transfer of a nucleic acid fragment into the genome of a host organism, resulting in genetically stable inheritance. In the present invention, the host cell's genome includes chromosomal and extrachromosomal (e.g. plasmid) genes. Host organisms containing the transformed nucleic acid fragments are referred to as "transgenic" or "recombinant" or "transformed" organisms.

The term "carbon substrate" refers to a carbon source capable of being metabolized by host organisms of the present invention, and particularly refers to carbon sources selected from, but not limited to, the group consisting of aliphatic carboxylic acids or dicarboxylic acids, monosaccharides, oligosaccharides, polysaccharides, and one-carbon substrates or mixtures thereof.

Nitriles particularly pertinent to the invention are nitriles of

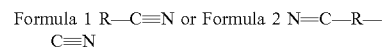

Formula 1 R—C≡N or Formula 2 N≡C—R—C≡N wherein N is Nitrogen, C is Carbon, and R is selected from the group consisting of: a) $C_1$–$C_9$ alkyl that is linear, branched or cyclic, optionally substituted with a hydroxyl group, an amino group, a carboxylic acid group, a carboxamide group, a halogen atom, or an oxo group; b) $C_1$–$C_9$ alkenyl, linear, branched or cyclic, optionally substituted with a hydroxyl group, an amino group, a carboxylic acid group, a carboxamide group, a halogen atom, or an oxo group; and c) $C_6$–$C_9$ aryl, optionally substituted with a hydroxyl group, an amino group, a carboxylic acid group, a carboxamide group, or a halogen atom. Particularly useful nitriles in the invention include, but are not limited to, acrylonitrile, methacrylonitrile, 3-hydroxypropionitrile, 3-hydroxybutyronitrile, 3-hydroxyvaleronitrile, butyronitrile, adiponitrile, benzonitrile, and glycolonitrile.

Additional nitriles particularly pertinent to the invention are nitriles of Formula 3:

$R^2$—C≡N                                   Formula 3 wherein N is Nitrogen, C is Carbon, and $R^2$ is selected from the group consisting of the general formulas 4, 5, 6, 7 and 8:

Formula 4

Formula 5

-continued

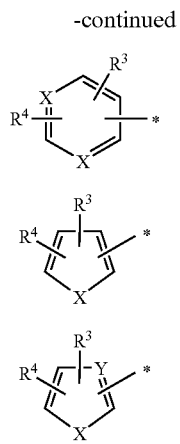

Formula 6

Formula 7

Formula 8 where in Formula 4, 5 and 6 X is N, in Formula 7 X is NH, O or S, and in Formula 8 X is NH and Y is N, O or S, and where $R^3$ and $R^4$ are, independently, selected from the group comprised of: a) a hydrogen atom, b) a halogen atom, c) a $C_1$–$C_9$ alkyl group that is linear, branched or cyclic and optionally substituted with a hydroxyl group, an amino group, a carboxylic acid group, a carboxamide group, a halogen atom, or an oxo group, d) a $C_1$–$C_9$ alkenyl group that is linear, branched or cyclic and optionally substituted with a hydroxyl group, an amino group, a carboxylic acid group, a carboxamide group, a halogen atom, or an oxo group, and e) a $C_6$–$C_9$ aryl, optionally substituted with a hydroxyl group, an amino group, a carboxylic acid group, a carboxamide group, or a halogen atom. Halogen atoms may be independently F, Cl, Br, or I. Particularly useful heterocyclic nitriles in the invention include, but are not limited to, 3-cyanopyridine, 4-cyanopyridine, pyrazinecarbonitrile, 2-furancarbonitrile, 2-thiophenecarbonitrile, and 4-thiazolecarbonitrile.

The terms "plasmid", "vector" and "cassette" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "altered biological activity" will refer to an activity, associated with a polypeptide (protein) encoded by a microbial nucleotide sequence which can be measured by an assay method, where that activity is either greater than or less than the activity associated with the native microbial sequence. "Enhanced biological activity" refers to an altered activity that is greater than that associated with the native sequence. "Diminished biological activity" is an altered activity that is less than that associated with the native sequence.

The terms "suitable aqueous reaction mixture" or "suitable reaction mixture" refer to the materials and water in which the nitrile and/or amide substrate and enzyme catalyst come into contact. Components of suitable aqueous reaction mixtures are referred to herein and those skilled in the art appreciate the range of component variations suitable for this process.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403–410 (1990), and DNASTAR (DNASTAR, Inc. 1228 S. Park St. Madison, Wis. 53715 USA), and the FASTA program incorporating the Smith-Waterman algorithm (W. R. Pearson, *Comput. Methods Genome Res.*, [Proc. Int. Symp.] (1994), Meeting Date 1992, 111–20. Editor(s): Suhai, Sandor. Publisher: Plenum, New York, N.Y.). The term "MEME" refers to a software program used to identify conserved diagnostic motifs based on a hidden Markov model (Timothy L. Bailey and Charles Elkan, *Fitting a mixture model by expectation maximization to discover motifs in biopolymers*, Proceedings of the Second International Conference on Intelligent Systems for Molecular Biology, pp. 28–36, AAAI Press, Menlo Park, Calif. (1994)). "MAST" (Timothy L. Bailey and Michael Gribskov, "Combining evidence using p-values: application to sequence homology searches" *Bioinformatics*, Vol. 14, pp. 48–54 (1998)) is a program that takes the output from the MEME program and searches the identified motifs against the protein databases such as EMBL and SwissProt. Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press Spring Harbor, N.Y. (1984) (hereinafter "Silhavy"); and by Ausubel, F. M. et al., *Current Protocols in Molecular Biology*, published by Greene Publishing Assoc. and Wiley-Interscience (1987) (hereinafter "Ausubel").

Sequence Identification

Comparison of the present amino acid sequences for the nitrile hydratase α and β-subunits and the amidase from *Comamonas testosteroni* 5-MGAM-4D to public databases revealed that the most similar-known sequences were all from *Pseudomonas putida* 5B (NRRL-18668; see: U.S. Pat. No. 5,811,286, and Wu et al., *Appl. Microbiol. Biotechnol.* 48:704–708 (1997)). The nitrile hydratase α-subunit was about 97.1% identical to the corresponding nitrile hydratase α-subunit from *P. putida* 5B (Table 1). The nitrile hydratase β-subunit was about 82.0% identical to the corresponding nitrile hydratase β-subunit from *P. putida* 5B. Lastly, the amidase was about 92.3% identical to the corresponding amidase from *P. putida* 5B.

TABLE 1

Sequence Analysis Results

| Gene Name | Similarity Identified | % Identity[a] | % Similarity[b] | E-value[c] | Citation |
|---|---|---|---|---|---|
| Amidase | Gi\|6225048\|sp\|O69768\| AMID_PSEPU | 92.3 | 92.5 | 0 | Wu et al., DNA Cell Biol. 17 (10), 915–920 (1998) |
| nitrile hydratase α-subunit | Gi\|2499193\|sp\|P97051\| NHAA_PSEPU | 97.1 | 97.1 | 10e-108 | Payne et al., Biochemistry 36 (18), |
| nitrile hydratase β-subunit | Gi\|2499195\|sp\|P97052\| NHAB_PSEPU | 82.0 | 82.5 | 6e-92 | Payne et al., Biochemistry 36 (18), 5447–5454 (1997) |

[a]Identity is defined as percentage of amino acids that are identical between the two proteins.
[b]Similarity is defined as percentage of amino acids that are identical or conserved between the two proteins.
[c]Expect value. The Expect value estimates the statistical significance of the match, specifying the number of matches, with a given score, that are expected in a search of a database of this size absolutely by chance.

Despite the sequence similarities between the nitrile hydratase and amidase enzymes of *Comamonas testosteroni* 5-MGAM-4D to those of *Pseudomonas putida* 5B (NRRL-18668), the accompanying Examples demonstrate that both the thermal stability, and stability under reaction conditions, of the *Comamonas testosteroni* 5-MGAM-4D nitrile hydratase enzyme (expressed in *E. coli* transformant SW132) are both different and markedly superior to the *Pseudomonas putida* 5B nitrile hydratase (expressed in *E. coli* transformant SW30, Wu et al., supra).

Identification of Homologs

The instant sequences may be employed as hybridization reagents for the identification of homologs. The basic components of a nucleic acid hybridization test include a probe, a sample suspected of containing the gene or gene fragment of interest, and a specific hybridization method. Probes of the present invention are typically single stranded nucleic acid sequences which are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration the shorter the hybridization incubation time needed. Optionally a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.*, 19:5143–5151, (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3M. If desired, one can add formamide to the hybridization mixture, typically 30–50% (v/v).

Various hybridization solutions can be employed. Typically, these comprise from about 20 to 60% volume, preferably 30%, of a polar organic solvent. A common hybridization solution employs about 30–50% v/v formamide, about 0.15 to 1M sodium chloride, about 0.05 to 0.1M buffers, such as sodium citrate, Tris-HCl, PIPES or HEPES (pH range about 6–9), about 0.05 to 0.2% detergent, such as sodium dodecylsulfate, or between 0.5–20 mM EDTA, FICOLL (about 300–500 kilodaltons), polyvinylpyrrolidone (about 250–500 kdal), and serum albumin. Also included in the typical hybridization solution will be unlabeled carrier nucleic acids from about 0.1 to 5 mg/mL, fragmented nucleic DNA, e.g., calf thymus or salmon sperm DNA, or yeast RNA, and optionally from about 0.5 to 2% wt./vol. glycine. Other additives may also be included, such as volume exclusion agents which include a variety of polar water-soluble or swellable agents, such as polyethylene glycol, anionic polymers such as polyacrylate or polymethylacrylate, and anionic saccharidic polymers, such as dextran sulfate.

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Microbial Recombinant Expression

The genes and gene products of the instant sequences may be produced in heterologous host cells, particularly in the cells of microbial hosts. Expression in recombinant microbial hosts may be useful for the expression of various pathway intermediates; for the modulation of pathways already existing in the host, or for the synthesis of new products heretofore not possible using the host.

Preferred heterologous host cells for expression of the instant genes and nucleic acid fragments are microbial hosts that can be found broadly within the fungal or bacterial families and which grow over a wide range of temperature, pH values, and solvent tolerances. For example, it is contemplated that any of bacteria, yeast, and filamentous fungi will be suitable hosts for expression of the present nucleic acid fragments. Because of transcription, translation and the protein biosynthetic apparatus is the same irrespective of the cellular feedstock, functional genes are expressed irrespective of carbon feedstock used to generate cellular biomass. Large-scale microbial growth and functional gene expression may utilize a wide range of simple or complex carbohydrates, organic acids and alcohols, saturated hydrocarbons such as methane or carbon dioxide in the case of photosynthetic or chemoautotrophic hosts. However, the functional genes may be regulated, repressed or depressed by specific growth conditions, which may include the form and amount of nitrogen, phosphorous, sulfur, oxygen, carbon or any trace micronutrient including small inorganic ions. In addition, the regulation of functional genes may be achieved by the presence or absence of specific regulatory molecules that are added to the culture and are not typically considered nutrient or energy sources.

Examples of host strains include but are not limited to bacterial, fungal or yeast species such as *Aspergillus, Trichoderma, Saccharomyces, Pichia, Candida, Hansenula, Salmonella, Bacillus, Acinetobacter, Zymomonas, Agrobacterium, Erythrobacter Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Methylobacterium, Alcaligenes, Synechocystis, Synechococcus, Anabaena, Thiobacillus, Methanobacterium, Klebsiella, Myxococcus,* and *Staphylococcus*. In another embodiment, suitable host strains are selected from the group consisting of *Aspergillus, Saccharomyces, Pichia, Candida, Hansuela, Bacillus, Rhodococcus, Streptomyces, Brevibacterium, Corynebacteria, Escherichia, Pseudomonas, Methylomonas, Synechocystis,* and *Klebsiella*. In a further embodiment, suitable host strains are selected from the group consisting of *Bacillus, Rhodococcus, Escherichia, Pseudomonas, Klebsiella,* and *Methylomonas*.

Microbial expression systems and expression vectors containing regulatory sequences that direct high level expression of foreign proteins are well known to those skilled in the art. Any of these could be used to construct chimeric genes for expression of the present nitrile hydratase, amidase, and PK7. These chimeric genes could then be introduced into appropriate microorganisms via transformation to provide high-level expression of the enzymes Accordingly it is expected, for example, that introduction of chimeric genes encoding the instant bacterial enzyme under the control of the appropriate promoter, will demonstrate increased nitrile to amide and/or carboxylic acid conversion. It is contemplated that it will be useful to express the instant genes both in natural host cells as well as in a heterologous host. Introduction of the present genes into native hosts will result in altered levels of existing nitrile hydratase and amidase activity. Additionally, the instant genes may also be introduced into non-native host bacteria where an existing nitrile-amide-carboxylic acid pathway may be manipulated.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the instant ORF in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara, tet, trp, $IP_L$, $IP_R$, T7, tac, and trc (useful for expression in *Escherichia coli*) as well as the amy, apr, npr promoters and various phage promoters useful for expression in *Bacillus*. Additionally, the deoxy-xylulose phosphate synthase or methanol dehydrogenase operon promoter (Springer et al., *FEMS Microbiol Lett* 160:119–124 (1998)), the promoter for polyhydroxyalkanoic acid synthesis (Foellner et al., *Appl. Microbiol. Biotechnol*. 40:284–291 (1993)), promoters identified from native plasmids in methylotrophs (EP 296484), promoters identified from methanotrophs (PCT/US03/33698), and promoters associated with antibiotic resistance [e.g., kanamycin (Springer et al., supra; Ueda et al., *Appl. Environ. Microbiol*. 57:924–926 (1991)) or tetracycline (U.S. Pat. No. 4,824,786)] are suitable for expression of the present coding sequences, especially in C1 metabolizers.

Termination control regions may also be derived from various genes native to the preferred hosts. Optionally, a termination site may be unnecessary; however, it is most preferred if included.

Methods of manipulating genetic pathways are common and well known in the art. Selected genes in a particularly pathway may be up-regulated or down-regulated by variety of methods. Additionally, competing pathways may be eliminated or sublimated by gene disruption and similar techniques.

Once a key genetic pathway has been identified and sequenced, specific genes may be up-regulated to increase the output of the pathway. For example, additional copies of the targeted genes may be introduced into the host cell on multicopy plasmids such as pBR322. Alternatively the target genes may be modified so as to be under the control of non-native promoters. Where it is desired that a pathway operate at a particular point in a cell cycle or during a fermentation run, regulated or inducible promoters may used to replace the native promoter of the target gene. Similarly, in some cases the native or endogenous promoter may be modified to increase gene expression. For example, endogenous promoters can be altered in vivo by mutation, deletion, and/or substitution (see, Kmiec, U.S. Pat. No. 5,565, 350; Zarling et al., PCT/US93/03868).

Alternatively, it may be necessary to reduce or eliminate the expression of certain genes in a pathway or in competing pathways that may serve as competing sinks for energy or carbon. Methods of down-regulating genes for this purpose have been explored. Where sequence of the gene to be disrupted is known, one of the most effective methods of gene down regulation is targeted gene disruption where foreign DNA is inserted into a structural gene so as to disrupt transcription. This can be effected by the creation of genetic cassettes comprising the DNA to be inserted (often a genetic marker) flanked by sequence having a high degree of homology to a portion of the gene to be disrupted. Introduction of the cassette into the host cell results in insertion of the foreign DNA into the structural gene via the native DNA replication mechanisms of the cell (Hamilton et al., *J. Bacteriol.* 171:4617–4622 (1989); Balbas et al., *Gene* 136: 211–213 (1993); Gueldener et al., *Nucleic Acids Res.* 24:2519–2524 (1996); and Smith et al., *Methods Mol. Cell. Biol.* 5:270–277(1996)).

Antisense technology is another method of down regulating genes where the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA which encodes the protein of interest. The person skilled in the art will know that special considerations are associated with the use of antisense technologies in order to reduce expression of particular genes. For example, the proper level of expression of antisense genes may require the use of different chimeric genes utilizing different regulatory elements known to the skilled artisan.

Although targeted gene disruption and antisense technology offer effective means of down regulating genes where the sequence is known, other less specific methodologies have been developed that are not sequence based. For example, cells may be exposed to a UV radiation and then screened for the desired phenotype. Mutagenesis with chemical agents is also effective for generating mutants and commonly used substances include chemicals that affect non-replicating DNA such as $HNO_2$ and $NH_2OH$, as well as agents that affect replicating DNA such as acridine dyes, notable for causing frameshift mutations. Specific methods for creating mutants using radiation or chemical agents are well documented in the art. (See for example, Thomas D. Brock in Biotechnology: *A Textbook of Industrial Microbiology*, Second Edition (1989) Sinauer Associates, Inc., Sunderland, Mass. (hereinafter "Brock"), or Deshpande, Mukund V., *Appl. Biochem. Biotechnol.*, 36:227 (1992) (hereinafter "Deshpande")).

Another non-specific method of gene disruption is the use of transposable elements or transposons. Transposons are genetic elements that insert randomly in DNA but can be latter retrieved on the basis of sequence to determine where the insertion has occurred. Both in vivo and in vitro transposition methods are known. Both methods involve the use of a transposable element in combination with a transposase enzyme. When the transposable element or transposon, is contacted with a nucleic acid fragment in the presence of the transposase, the transposable element will randomly insert into the nucleic acid fragment. The technique is useful for random mutagenesis and for gene isolation, since the disrupted gene may be identified on the basis of the sequence of the transposable element. Kits for in vitro transposition are commercially available (see for example The Primer Island Transposition Kit, available from Perkin Elmer Applied Biosystems, Branchburg, N.J., based upon the yeast Ty1 element; The Genome Priming System, available from New England Biolabs, Beverly, Mass.; based upon the bacterial transposon Tn7; and the EZ::TN Transposon Insertion Systems, available from Epicentre Technologies, Madison, Wis., based upon the Tn5 bacterial transposable element).

Industrial Production of Biocatalyst

Commercial production of biocatalyst for preparing amides using transformants harboring the nitrile hydratase catalyst disclosed herein (encoded by genes for the α- and β-subunits, and optionally, accessory protein P7K) and for preparing carboxylic acids from amides using the amidase catalyst disclosed herein may be conducted using a variety of culture methodologies. Large-scale production of a specific gene product may be produced by both batch and continuous culture methodologies.

A classical batch culturing method is a closed system where the composition of the media is set at the beginning of the culture and not subject to artificial alterations during the culturing process. Thus, at the beginning of the culturing process the media is inoculated with the desired organism or organisms and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable in the present invention and comprise a typical batch system with the exception that the substrate is added in increments as the culture progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch culturing methods are common and well known in the art and examples may be found in Brock (supra) and Deshpande (supra).

Commercial production of biocatalysts may also be accomplished with a continuous culture. Continuous cultures are an open system where a defined culture media is added continuously to a bioreactor and an equal amount of conditioned media is removed simultaneously for processing. Continuous cultures generally maintain the cells at a constant high-liquid-phase density where cells are primarily in log phase growth.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Fermentation media in the present invention must contain suitable carbon substrates. Suitable substrates may include but are not limited to aliphatic carboxylic acid and dicarboxylic acids (such as lactic acid or succinic acid), glycerol, monosaccharides (such as glucose and fructose), disaccharides (such as lactose or sucrose), oligosaccharides (such as soluble starch), polysaccharides (such as starch or cellulose or mixtures thereof), and unpurified mixtures from renewable feedstocks (such as cheese whey permeate, cornsteep liquor, sugar beet molasses, and barley malt). Additionally the carbon substrate may also be one-carbon substrates such as carbon dioxide, methane or methanol for which metabolic conversion into key biochemical intermediates has been demonstrated. In addition to one and two carbon substrates, methylotrophic organisms are also known to utilize a number of other carbon-containing compounds such as methylamine, glucosamine, and a variety of amino acids for metabolic activity. For example, methylotrophic yeast are known to utilize the carbon from methylamine to form trehalose or glycerol (Bellion et al., *Microb. Growth C1 Compd.*, [Int. Symp.], 7th (1993), 415–32. Editor(s): Murrell, J. Collin; Kelly, Don P. Publisher: Intercept, Andover, UK). Similarly, various species of *Candida* will metabolize alanine or oleic acid (Sulter et al., *Arch. Microbiol.* 153: 485–489 (1990)). Therefore, it is contemplated that the source of carbon utilized in the present invention may encompass a wide variety of carbon-containing substrates and will only be limited by the microorganism employed.

Biocatalytic Conversion of Nitriles to Amides or Carboxylic Acids

An aqueous reaction mixture containing the aliphatic, aromatic, or heterocyclic aromatic nitrile is prepared by mixing the nitrile with an aqueous suspension of the appropriate enzyme catalyst. Intact microbial cells can be used as catalyst without any pretreatment, such as permeabilization or heating. Alternatively, the cells can be immobilized in a polymer matrix (e.g., alginate, carrageenan, polyvinyl alcohol, or polyacrylamide gel (PAG)) or on a soluble or insoluble support (e.g., celite, silica) to facilitate recovery and reuse of the catalyst. Methods to immobilize cells in a polymer matrix or on a soluble or insoluble support have been widely reported and are well known to those skilled in the art. The enzyme can also be isolated from the microbial cells and used directly as catalyst, or the enzyme can be immobilized in a polymer matrix or on a soluble or insoluble support. These methods have also been widely reported and are well known to those skilled in the art (*Methods in Biotechnology*, Vol. 1: Immobilization of Enzymes and Cells; Gordon F. Bickerstaff, Editor; Humana Press, Totowa, N.J., USA; 1997).

Intact microbial cells, either immobilized or unimmobilized, containing genes that encode a polypeptide having nitrile hydratase activity or amidase activity, or containing genes that encode a combination of polypeptides separately having nitrile hydratase and amidase activities, can be used as catalyst without any pretreatment, such as permeabilization, freeze thawing or heating. Alternatively, the microbial cells may be permeabilized by methods familiar to those skilled in the art (e.g., treatment with toluene, detergents, or freeze-thawing) to improve the rate of diffusion of materials into and out of the cells. Methods for permeabilization of microbial cells are well-known to those skilled in the art (Felix, H., *Anal. Biochem.*, 120:211–234 (1982)).

Some of the aliphatic or aromatic nitriles used as starting material in the present invention are only moderately water soluble. Their solubility also depends on the temperature of the solution and the salt concentration in the aqueous phase; the optional inclusion of a buffer, or the production of the ammonium salt of a carboxylic acid by hydrolysis of the corresponding amide are two possible sources of salt in a reaction mixture. In the present case, producing a hydrated or hydrolyzed reaction product at a concentration greater than the solubility limit of the starting aliphatic or aromatic nitrile is accomplished using a reaction mixture that is initially composed of two phases: an aqueous phase (containing the enzyme catalyst and dissolved aliphatic or aromatic nitrile) and an organic phase (the undissolved aliphatic or aromatic nitrile, optionally dissolved in an organic solvent not miscible with the aqueous phase). As the reaction progresses, the aliphatic or aromatic nitrile dissolves into the aqueous phase, eventually yielding a product mixture which may be a single phase, depending on the solubility of the products in water, and on the presence or absence of an optional organic solvent not miscible with water.

The aqueous phase of a two-phase reaction mixture can contain, at a minimum, only as much water as is sufficient to result in a) complete conversion of the aliphatic or aromatic nitrile to the corresponding amide or carboxylic acid (dependent on whether only active nitrile hydratase or a combination of active nitrile hydratase and amidase enzyme are present), and b) maintenance of the hydrolytic activity of the enzyme catalyst. The reaction may also be run by adding the aliphatic or aromatic nitrile to the reaction mixture at a rate approximately equal to the enzymatic hydration or hydrolysis reaction rate, thereby maintaining a single-phase aqueous reaction mixture, thereby avoiding the potential problem of substrate inhibition of the enzyme at high starting material concentrations.

The final concentration of aliphatic or aromatic amide or carboxylic acid in solution in the product mixture at complete conversion of the corresponding aliphatic or aromatic nitrile may range from 0.001 M to the solubility limit of the aliphatic or aromatic nitrile in the product mixture. Product may precipitate from the reaction mixture during the course of the reaction, allowing for the production of amide or carboxylic acid in excess of the solubility of said product in the reaction mixture. Typically, the concentration of the aliphatic or aromatic amide or carboxylic acid product in solution in the product mixture ranges from 0.001 M to 7.0 M. The aliphatic or aromatic amide or carboxylic acid may also be isolated from the product mixture (after removal of the catalyst) by optionally adjusting the pH of the reaction mixture to between 2.0 and 2.5 with concentrated HCl when the product of the reaction is a carboxylic acid, saturating the resulting solution with sodium chloride, and extracting the aliphatic or aromatic amide or carboxylic acid with a suitable organic solvent, such as ethyl acetate, ethyl ether, methyl isobutyl ketone or dichloromethane. The organic extracts are then combined, stirred with a suitable drying agent (e.g., magnesium sulfate), filtered, and the solvent removed (e.g., by rotary evaporation) to produce the desired product in high yield and in high purity (typically 98–99% pure). If desired, the product can be further purified by recrystallization or distillation.

The concentration of enzyme catalyst in the reaction mixture depends on the specific catalytic activity of the enzyme catalyst and is chosen to obtain the desired rate of reaction. The wet cell weight of the microbial cells used as catalyst in hydrolysis reactions typically ranges from 0.001 grams to 0.300 grams of wet cells per mL of total reaction volume, preferably from 0.002 grams to 0.050 grams of wet cells per mL; the cells may be optionally immobilized as described above. The specific activity of the microbial cells (IU/gram dry cell weight) is determined by measuring the rate of conversion of a 0.10–0.50 M solution of a nitrile substrate to the desired amide or carboxylic acid product at 25° C., using a known weight of microbial cell catalyst. An IU of enzyme activity is defined as the amount of enzyme activity required to convert one micromole of substrate to product per minute.

The temperature of the hydrolysis reaction is chosen to optimize both the reaction rate and the stability of enzyme catalyst. The temperature of the reaction may range from just above the freezing point of the reaction mixture (ca. 0° C.) to 65° C., with a preferred range of reaction temperature of from 5° C. to 45° C. An enzyme catalyst solution or suspension may be prepared by suspending the unimmobilized or immobilized cells in distilled water, or in an aqueous reaction mixture of a buffer that will maintain the initial pH of the reaction between 5.0 and 10.0, preferably between 6.0 and 8.0, or by suspending the immobilized enzyme catalyst in a similar mixture, or by preparing a solution of a cell extract, partially purified or purified enzyme(s), or a soluble form of the immobilized enzymes in a similar mixture. After the nitrile is added and as the reaction proceeds, the pH of the reaction mixture may change due to the formation of an ammonium salt of the carboxylic acid from the corresponding nitrile functionality of the aliphatic or aromatic nitrile (when using a combination of nitrile hydratase and amidase enzymes). The reaction can be run to completely convert the nitrile with no pH control, or a suitable acid or base can be added over the course of the reaction to maintain the desired pH.

EXAMPLES

The present invention is further defined in the following Examples that indicate preferred embodiments of the invention. From the above discussion and these Examples, one skilled in the art can ascertain the essential characteristics of this invention, and without departing from the spirit and scope thereof, can make various changes and modifications of the invention to adapt it to various uses and conditions.

In the following Examples, the percent recovery of nitrile, and the percent yields of the corresponding amide and carboxylic acid products were based on the initial concentration of nitrile present in the reaction mixture, and were determined by HPLC. Analyses of 3-hydroxyvaleronitrile, adiponitrile, butyronitrile, benzonitrile, and methacrylonitrile were performed by HPLC using a refractive index detector in combination with a Supelco LC-18-DB column (15 cm×4.6 mm diameter) with precolumn at 25° C. and 10 mM acetic acid, 10 mM sodium acetate in 7.5% methanol in water as eluent at 1.5 mL/min. Analyses for glycolonitrile, acrylonitrile, 3-HPN, 3-HBN, and their corresponding reaction products were performed by HPLC using a Bio-Rad HPX-87H organic acid analysis column (30 cm×7.8 mm dia.) with precolumn at 50° C. and 0.010 N $H_2SO_4$ as eluent at 1 mL/min. Analyses for 3-cyanopyridine, pyrazinecarbonitrile, 2-furancarbonitrile, 2-thiophenecarbonitrile, 4-thiazolecarbonitrile and their corresponding reaction products, were performed by HPLC using a UV detector at 254 nm in combination with a 10-cm×4-mm ID, 5 μm C8 Discovery column (Supelco) with precolumn, 1.0 mL/min of 5% $CH_3CN$/95% 10 mM NaOAc, 10 mM AcOH as solvent, and N,N-dimethylbenzamide as external standard.

General Methods

Standard recombinant DNA and molecular cloning techniques used in the Examples are well known in the art and are described by Maniatis (supra) and Ausubel (supra).

Materials and methods suitable for the maintenance and growth of bacterial cultures are well known in the art. Techniques suitable for use in the following examples may be found as set out in *Manual of Methods for General Bacteriology* (Phillip Gerhardt, R. G. E. Murray, Ralph N. Costilow, Eugene W. Nester, Willis A. Wood, Noel R. Krieg and G. Briggs Phillips, eds., American Society for Microbiology, Washington, D.C. (1994)) or in Brock, supra.

The following abbreviations in the specification correspond to units of measure, techniques, properties, or compounds as follows: "sec" means second(s), "min" means minute(s), "h" means hour(s), "d" means day(s), "mL" means milliliters, "L" means liters, "mM" means millimolar, "M" means molar, "mmol" means millimole(s), "rpm" means revolutions per minute, "slpm" means standard liters per minute, "psig" means pounds per square inch, and "wt" means weight. "HPLC" means high performance liquid chromatography, "ca" means approximately, "O.D." means optical density at the designated wavelength, "dcw" means dry cell weight, and "IU" means International Units.

Example 1

Identification of a Genomic DNA Fragment Encoding *C. testosteroni* 5-MGAM-4D Nitrile Hydratase

*Comamonas testosteroni* 5-MGAM-4D (ATCC 55744) was grown in LB media at 37° C. with shaking. Genomic DNA was prepared using a Puregene DNA Isolation Kit according to the manufacturer (Gentra Systems, Minneapolis, Minn.). A Southern analysis (Southern et al., *J. Mol. Biol.*, 98:503 (1975)) was performed on EcoRI restricted genomic DNA using *Psuedomonas putida* NRRL-18668 genes (SEQ ID NOs:1 and 2) encoding nitrile hydratase alpha and beta subunits (U.S. Pat. No. 5,811,286) as probes. Probe labeling, hybridization, and detection were done using ECL random prime labeling and detection systems version II according to the manufacturer (Amersham International, Buckinghamshire, UK). The alpha (SEQ ID NO:1) and beta (SEQ ID NO:2) probes each showed positive hybridization to the same 5.7 kb EcoRI DNA fragment.

Example 2

Cloning of a Genomic DNA Fragment Encoding *C. testosteroni* 5-MGAM-4D Nitrile Hydratase Genomic DNA from *C. testosteroni* 5-MGAM-4D was prepared (Example 1), restricted with EcoRI, and subjected to standard agarose gel electrophoresis. DNA fragments in the size range of approximately 5–7 kb were isolated and ligated to EcoRI restricted pUC19 (New England Biolabs, Beverly, Mass.). This plasmid library was plated and screened with the *P. putida* NRRL-18668 nitrile hydratase α-subunit gene probe (SEQ ID NO:1). Probe labeling, hybridization and detection were done using ECL random prime labeling and detection systems version II according to the manufacturer (Amersham International). A positively hybridizing colony was isolated and determined to contain an insert of 5.7 kb (pKP57).

Example 3

Determination of the Nucleotide Sequence of the Genes Encoding *C. testosteroni* 5-MGAM-4D Nitrile Hydratase The nucleotide sequence of the pKP57 (EXAMPLE 2) insert was determined using an ABI 377-XL DNA sequencer and BigDye Terminator Cycle Sequencing chemistry. A BlastN analysis (Altschul et al., *Nucleic Acids Res.*, 25:3389–3402 (1997)) of the obtained sequence to the GenBank® database confirmed the presence of complete genes encoding nitrile hydratase α and β-subunits and a partial gene encoding amidase. Nucleotide sequences of the pKP57 insert encoding nitrile hydratase α- and β-subunits are given in SEQ ID NO:3 and SEQ ID NO:5, respectively. Deduced amino acid sequences of the pKP57 insert for the α- and β-subunits are given in SEQ ID NO:4 and SEQ ID NO:6, respectively.

BlastP analysis was conducted using the deduced amino acid sequence for the nitrile hydratase α- and β-subunits. Results are shown in Table 1. The closest match to the instant amino acid sequence of the nitrile hydratase α-subunit was the nitrile hydratase α-subunit from *Pseudomonas putida* NRRL-18668 (97.1% identity, 97.1% similarity, E value=10e$^{-108}$). The closest match to the instant amino acid sequence of the nitrile hydratase β-subunit was the nitrile hydratase β-subunit from *Pseudomonas putida* NRRL-18668 (82.0% identity, 82.5% similarity, E value=6e$^{-92}$).

Example 4

Production of *C. testosteroni* 5-MGAM-4D Nitrile Hydratase in *E. coli*

A DNA fragment encoding the nitrile hydratase alpha and beta subunits from *C. testosteroni* 5-MGAM-4D (SEQ ID NO:7) was obtained from pKP57 by standard PCR via a GeneAmp Kit according to the manufacturer (Roche, Branchburg, N.J.) using Primer 1 (SEQ ID NO:8) and Primer 2 (SEQ ID NO:9) and subcloned into pGEM-T (Promega, Madison, Wis.) under control of the T7 promoter to generate pSW131. *E. coli* BL21(DE3) (Novagen, Madison, Wis.) was transformed with pSW131 using standard procedures. Growth and induction of *E. coli* BL21 (DE3) harboring pSW131 was carried out essentially as recommended by Novagen. Modifications included the addition of cobalt chloride and sodium citrate at the time of induction to a final concentration of 0.01 mg/ml and 0.1 mg/ml respectively. Induction was carried out at 30 C for 16 hrs. Production of alpha (23 kDa) and beta (24 kDa) proteins was confirmed by standard SBS-PAGE analysis.

Example 5

Conversion of 3-hydroxyvaleronitrile (3-HVN) by Transformed *E. coli*

Growth and induction of *E. coli* BL21 (DE3) cells harboring pSW131 was carried out as described in EXAMPLE 4. Cells were then harvested by centrifugation, washed twice in buffer (0.1 M potassium phosphate pH 7.0) and suspended at 100 mg wet cells/ml in buffer. The nitrilase activity assay mix included cells (50 mg/mL), 3-hydroxyvaleronitrile (0.3 M) and buffer (0.1 M potassium phosphate, pH 7.0) stirred at ambient temperature. HPLC analysis demonstrated 17% conversion of 3-HVN to the corresponding amide(3-hydroxyvaleramide) in 15 min.

Example 6

Production of High-Level *C. testosteroni* 5-MGAM-4D Nitrile Hydratase Activity in *E. coli* Requires Downstream Sequence A plasmid (pSW132; ATCC PTA-5073), containing a DNA fragment encoding the *C. testosteroni* 5-MGAM-4D nitrile hydratase alpha and beta subunits plus 0.9 kb of downstream DNA encoding the accessory protein P7K (SEQ ID NO:11) under control of the T7 promoter was constructed by replacing the smaller BamHI/PstI fragment in pSW131 with the corresponding BamHI/PstI fragment from pKP57. *E. coli* BL21 (DE3) (Novagen) was transformed with pSW132 using standard procedures. Growth and induction of *E. coli* BL21(DE3) harboring pSW132 ("*E. coli* strain SW132") was carried out as described in EXAMPLE 4, and production of alpha and beta proteins was confirmed by standard SDS-PAGE analysis.

A DNA fragment (SEQ ID NO:11) encoding the *C. testosteroni* 5-MGAM-4D nitrile hydratase alpha and beta subunits plus 0.9 kb of downstream DNA encoding the accessory protein P7K was also obtained from pKP57 by standard PCR via a GeneAmp Kit according to the manufacturer (Roche) using Primer 1 (SEQ ID NO:8) and Primer 3 (SEQ ID NO:12) and subcloned into pTrcHis2-TOPO under control of the trc promoter to generate pSW137 in *E. coli* TOP10 according to the manufacturer (Invitrogen). Growth and induction of *E. coli* TOP10 harboring pSW137 was carried out as described in EXAMPLE 4, and production of alpha and beta proteins was confirmed by standard SDS-PAGE analysis. Production of the alpha and beta proteins in *E. coli* BL21(DE3) harboring pSW132 and in *E. coli* TOP10 harboring pSW137 was qualitatively indistinguishable to that obtained from *E. coli* BL21 (DE3) harboring pSW131 (EXAMPLE 4).

Growth and induction of *E. coli* BL21(DE3) harboring pSW132 was carried out as described in EXAMPLE 4. Cells were then harvested by centrifugation, washed twice in buffer (0.1 M potassium phosphate pH 7.0) and suspended at 100 mg wet cells/ml in buffer. The nitrile hydratase activity assay mix included cells (2 mg/mL), 3-hydroxyvalerontrile (0.3 M) and buffer (0.1 potassium phosphate, pH 7.0) stirred at ambient temperature. HPLC analysis demonstrated 100% conversion of 3-hydroxyvaleronitrile to 3-hydroxyvaleramide in 5 min. Similarly, nitrile hydratase activity assay of *E. coli* TOP10 harboring pSW137 demonstrated 100% conversion of 3-hydroxyvaleronitrile to 3-hydroxyvaleramide in 5 min. Comparing these results to those obtained from pSW131 (Example 5) demonstrated the importance of the DNA downstream of the nitrile hydratase beta gene, in obtaining maximal nitrile hydratase activity (Table 2). The downstream nucleotide sequence (SEQ ID NO:10) contains a small open reading frame, the sequence of which is given in SEQ ID NO:13. The deduced amino acid sequence (called P7K) is given in SEQ ID NO:14.

TABLE 2

Comparison of Expression Vectors pSW131 and pSW132

| Expression Vector | Expressed Genetic Components from C. testosteroni 5-MGAM-4D | % Conversion of 0.35M 3-HVN to 3-HVAm at Room Temperature |
|---|---|---|
| PSW131 | Nitrile hydratase α- and β-subunits | 17% in 15 min |
| PSW132 | Nitrile hydratase α- and β-subunits plus accessory protein "P7K" | 100% in 5 min |

Example 7

Determination of the Nucleotide Sequence of the Gene Encoding C. testosteroni 5-MGAM-4D Amidase Genomic DNA from C. testosteroni 5-MGAM-4D was prepared (EXAMPLE 1), restricted with PstI, and subjected to Southern analysis using a standard PCR product comprising the first 0.6 kb of the pKP57 (EXAMPLE 2) insert as a probe (SEQ ID NO:15). Probe labeling, hybridization and detection were done using ECL random prime labeling and detection systems version II according to the manufacturer (Amersham International). This probe gave hybridized to a 2.4 kb PstI fragment. Genomic DNA digested with PstI was subjected to standard agarose gel electrophoresis. DNA fragments in the size range of approximately 2–4 kb were isolated and ligated into PstI restricted pUC19. This plasmid library was plated and screened with the same 0.6 kb probe (SEQ ID NO:15). Probe labeling, hybridization and detection were done using ECL random prime labeling and detection systems version II according to the manufacturer (Amersham International). A positively hybridizing colony was isolated and determined to contain an insert of 2.4 kb (pKP59).

Nucleotide sequencing confirmed that the insert is a DNA fragment that overlaps the EcoRI DNA fragment previously cloned (pKP57). Thus, by combining the nucleotide sequences from pKP57 and pKP59, the complete nucleotide sequence for the amidase gene was determined (SEQ ID NO:16). The deduced amidase amino acid sequence is given in SEQ ID NO:17. The nucleotide sequence of a 7.4 kb DNA fragment from C. testosteroni 5-MGAM-4D comprising complete coding sequences for amidase and nitrile hydratase is given in SEQ ID NO:18.

BlastP analysis was conducted using the deduced amidase amino acid sequence (SEQ ID NO:17; Table 1). The closest publicly known match was to that of the amidase from Pseudomonas putida NRRL-18668 (92.3% identity, 92.5% similarity, E value=0).

Example 8

Production of C. testosteroni 5-MGAM-4D Amidase in E. coli

A DNA fragment encoding the amidase from C. testosteroni 5-MGAM-4D was obtained from genomic DNA by standard PCR via a GeneAmp Kit according to the manufacturer (Roche), using Primer 4 (SEQ ID NO:19) and Primer 5 (SEQ ID NO:20) and subcloned into pGEM-T (Promega) under control of the T7 promoter to generate pKP60. E. coli BL21 (DE3) (Novagen) was transformed with pKP60 using standard procedures. Growth and induction of E. coli BL21 (DE3) harboring pKP60 was carried out according to Novagen, and production of amidase protein was confirmed by standard SDS-PAGE analysis A DNA fragment encoding the amidase from C. testosteroni 5-MGAM-4D was also obtained by standard PCR using Primer 6 (SEQ ID NO:21) and Primer 7 (SEQ ID NO:22) and subcloned into pTrcHis2 TOPO under control of the trc promoter to generate pSW133 in E. coli TOP10 according to the manufacturer (Invitrogen). Growth and induction of E. coli TOP10 harboring pSW133 was carried out according to Invitrogen, and production of amidase protein was confirmed by standard SDS-PAGE analysis.

Example 9

Co-Production of C. testosteroni 5-MGAM-4D Nitrile Hydratase and Amidase in E. coli A DNA fragment encoding the amidase, NHase alpha and beta, and accessory protein P7K from C. testosteroni 5-MGAM-4D (SEQ ID NO:23) was obtained from genomic DNA by standard PCR via a GeneAmp Kit according to the manufacturer (Roche), using Primer 6 (SEQ ID NO:21) and Primer 3 (SEQ ID NO:12), and subcloned into pTrcHis2-TOPO (Invitrogen) under control of the Trc promoter to generate pSW136.

Example 10

Fermentation of Escherichia coli SW132 Cells

The production of nitrile hydratase in a 14 L Braun Biostat C fermentor (B. Braun Biotech International Gmbh, Melsungen, Germany) was made in mineral medium with glucose, ammonia, and yeast extract. E. coli strain SW132 (E. Coli BL21(DE3) harboring plasmid pSW132 as described in Example 6) was grown in a seed culture for 10 h prior to inoculation of the fermentor. IPTG (1 mM) was added to the fermentor at 30–35 $OD_{\lambda=550}$ and cells were harvested 5 h after IPTG addition. Fermentation protocol: vessel medium was prepared in an initial batch of 7.5 L containing 32 g $KH_2PO_4$, 8.0 g $MgSO_4.7H_2O$, 8.0 g $(NH_4)_2SO_4$, 50 g yeast extract, and 10 mL Mazu DF204 antifoam (BASF Corporation, Mount Olive, N.J.). Following sterilization, 369 g glucose solution (60% w/w), 160 mL trace element solution (Table 3), and 100 mg/L ampicillin were added. $NH_4OH$ (40% w/v) and 20% w/v $H_2SO_4$ were used for pH control. The set points for agitation, aeration, pH, pressure, dissolved oxygen concentration (DO), and temperature are described in Table 4 below. The dissolved oxygen concentration was controlled at 25% of air saturation with the agitation to rise first with increase oxygen demand and the aeration to follow. The 500 mL seed culture was grown in a 2 L flask at 36° C., 300 rpm for 10 h to an $OD_{\lambda=550}$ of >2.0. In the fermentor at culture densities of 20–30 OD additional AMP was added to 100 mg/L. IPTG was added to 1 mM at culture densities of 30–35 OD. Glucose feed was started at <5 g/L and the scheduled rates are described in Table 5. Glucose feed rate was reduced if glucose accumulated above 2 g/L. Five hours after IPTG addition the cells were chilled to 5–10° C. and harvested by centrifugation; 490 g (wet cells) was harvested. The kinetics of growth and nitrile hydratase production are presented in Table 6.

TABLE 3

Trace elements solution:

| Chemical | Concentration g/L |
| --- | --- |
| Citric acid | 10.0 |
| $CaCl_2*2H_2O$ | 1.50 |
| $FeSO_4*7H_2O$ | 5.00 |
| $ZnSO_4*7H_2O$ | 0.39 |
| $CuSO_4*5H_2O$ | 0.38 |
| $CoCl_2*6H_2O$ | 0.20 |
| $MnCl_2*4H_2O$ | 0.30 |

TABLE 4

Fermentation Run Conditions

| | Initial Set-Point | Minimum | Maximum |
| --- | --- | --- | --- |
| Stirrer (rpm) | 400 | 400 | 850 |
| Airflow (slpm) | 2 | 2 | 16 |
| pH | 6.8 | 6.8 | 6.8 |
| Pressure (psig) | 0.5 | 0.5 | 0.5 |
| DO | 25% | 25% | 25% |
| Temp. C. | 36 | 36 | 36 |

TABLE 5

Glucose feed protocol

| Time, h | Rate (g/min) |
| --- | --- |
| 0–2 | 0.39 |
| 2–8 | 0.78 |
| 8–End | 0.60 |

TABLE 6

The kinetics of growth and nitrile hydratase production

| Time, h | $OD_{\lambda=550}$ | Glucose (g/L) | Nitrile Hydratase Production (U/g dry cell wt.) |
| --- | --- | --- | --- |
| 2.9 | 5.8 | 26.2 | |
| 4.9 | 15.7 | 20.2 | |
| 6.3 | 28 | 8.5 | 9157 |
| 8.1 | 44 | 6 | 10220 |
| 11.2 | 57.6 | 0.04 | 10888 |

Example 11

Hydration of Nitriles to Corresponding Amides by Unimmobilized E. coli SW132 Cells To a 20-mL reaction vessel equipped with magnetic stirring was added 0.04, 0.4, 2.0, or 5.0 mmol of acrylonitrile, methacrylonitrile, 3-hydroxypropionitrile, 3-hydroxybutyronitrile, 3-hydroxyvaleronitrile, butyronitrile, adiponitrile, benzonitrile, or glycolonitrile and distilled, deionized water was added to adjust the final volume of the mixture to 3.0 mL. To the reaction vessel was next added 1.0 mL of an aqueous suspension of 0.44–8.8 mg dry cell weight (dcw)/mL of E. coli SW132 cells (prepared as described in Example 10) in 0.10 M potassium phosphate buffer (pH 7.0, except for glycolonitrile, which was run at pH 6.0), and the mixture was stirred at 25° C. Samples (0.100 mL) of the reaction mixture were mixed with 0.400 mL of water, and then 0.200 mL of the diluted sample was either (a) mixed with 0.200 mL of 0.200 M sodium butyrate (acrylonitrile and 3-hydroxyvaleronitrile HPLC standard), 0.200 M N-ethylacetamide(methacrylonitrile HPLC standard), 0.200 M isobutyric acid (butyronitrile and 3-hydroxypropionitrile HPLC standard), or 0.200 M malonic acid (3-hydroxybutyronitrile HPLC standard) in water, or (b) measured against a calibration curve for product at 100% nitrile conversion (5-cyanovaleramide, adipamide, benzamide, glycolamide). The resulting mixture was centrifuged, and the supernatant analyzed by HPLC.

All reactions produced only the amide as the hydration product at 100% conversion of nitrile, with no hydrolysis of the nitrile to the corresponding carboxylic acid.

TABLE 7

Hydration of Nitriles to Corresp. Amides by E. coli SW132 Cells

| Nitrile | conc. (M) | mg dcw/mL | time (h) | amide | Amide yield (%) |
| --- | --- | --- | --- | --- | --- |
| Acrylonitrile | 0.50 | 2.2 | 3 | acrylamide | 100 |
| Acrylonitrile | 1.25 | 8.8 | 5 | acrylamide | 98 |
| Methacrytonitrile | 0.50 | 2.2 | 20 | methacrylamide | 100 |
| 3-hydroxypropionitrile | 0.50 | 2.2 | 3 | 3-hydroxypropionamide | 100 |
| 3-hydroxybutyronitrile | 0.50 | 4.4 | 4 | 3-hydroxybutryamide | 99 |
| 3-hydroxyvaleronitrile | 0.51 | 2.2 | 1 | 3-hydroxyvaleramide | 99 |
| Butyronitrile | 0.50 | 2.2 | 16 | butyramide | 100 |
| Adiponitrile | 0.50 | 0.44 | 1.5 | 5-cyano-valeramide | 93 |
| | | | | adipamide | 8 |
| Adiponitrile | 0.50 | 4.4 | 1 | adipamide | 100 |
| Benzonitrile | 0.010 | 2.2 | 2 | benzamide | 99 |
| Glycolonitrile | 0.10 | 2.2 | 2 | glycolamide | 63 |

Example 12

Hydration of 3-Hydroxyvaleronitrile Using a Partially-Purified Protein Extract of E. coli SW132 Cells E. coli SW132 cells (0.4874 g) were suspended in 2.0 mL of cold breaking buffer consisting of 1 mM DTT and 0.1 mM PMSF in 0.1 M potassium phosphate buffer (pH 7). The suspension (200 mg wet cell weight/mL) was loaded in a French Pressure Mini Cell, and the cells were ruptured at 16000–17000 psi. Cell debris was removed from the resulting mixture by centrifugation at 38000 RCF for 15 min. Approximately 1.68 mL of extract supernatant was recovered, having a nitrile hydratase activity equivalent to a 199 mg wet cell weight/mL cell suspension.

To a 20-mL reaction vessel equipped with magnetic stirring was added 0.4 mL of the E. coli SW132 extract supernatant, 0.6 mL of deionized water, and 3 mL of 0.667 M 3-hydroxyvaleronitrile in water. The mixture was stirred at 25° C. Samples (0.100 mL) of the reaction mixture were mixed with 0.100 mL of water, and then 0.200 mL of the diluted sample was mixed with 0.200 mL of 0.200 M sodium butyrate (external standard) and analyzed by HPLC. After 120 min, the yield of 3-hydroxyvaleramide was 99% at 100% conversion of 3-hydroxyvaleronitrile.

Example 13

Comparison of Thermal Stability of Nitrile Hydratase from *Comamonas testosteroni* 5-MGAM-4D and *Pseudomonas putida* 5B Cells A 44 mg dry cell weight/mL suspension of either *E. coli* SW30 wet cells (having active nitrile hydratase from *Pseudomonas putida* 5B) or *E. coli* SW132 wet cells (having active nitrile hydratase from *Comamonas testosteroni* 5-MGAM-4D) in 0.50 M phosphate buffer was heated to 50° C. in a water bath. At predetermined times, aliquots of the 50° C. cell suspensions were rapidly cooled to 25° C. in a water bath, and these suspensions were assayed for remaining nitrile hydratase activity by adding 1.0 mL aliquots of the heated/cooled cell suspensions with stirring to 3.0 mL of 0.667 M 3-hydroxyvaleronitrile in water at 25° C. Samples (0.100 mL) of the reaction mixture were withdrawn at predetermined times and mixed with 0.100 mL of water, then 0.200 mL of the diluted sample was mixed with 0.200 mL of 0.200 M sodium butyrate (external standard), centrifuged, and the supernatant and analyzed by HPLC. The rate of hydration of 3-hydroxyvaleronitrile in each reaction was determined, and remaining nitrile hydratase specific activity of the cells calculated. The nitrile hydratase specific activity and % of enzyme recovered for *E. coli* SW30 and *E. coli* SW132, respectively, as a function of time at 50° C. is listed in Table 8, below.

TABLE 8

Comparison of *E. coli* SW30 and *E. coli* SW132 Nitrile Hydratase Thermostability.

| Time At 50° C. (min) | SW30 Nitrile Hydratase (IU/g dcw) | Nitrile Hydratase Recovery (%) | SW132 Nitrile Hydratase (IU/g dcw) | Nitrile Hydratase Recovery (%) |
|---|---|---|---|---|
| 0 | 103 | 100 | 7752 | 100 |
| 30 | 1.6 | 1.6 | 6940 | 90 |
| 60 | 0 | 0 | 6437 | 83 |

Example 14

Comparison of *Comamonas testosteroni* 5-MGAM-4D and *Pseudomonas putida* 5B Nitrile Hydratase for Hydration of Acrylonitrile to Acrylamide To a 20-mL reaction vessel (equipped with magnetic stirring) was added 0.270 g (5.1 mmol) of acrylonitrile and a suspension of either 107.6 mg dry cell weight *E. coli* SW30 wet cells (expressing the active nitrile hydratase from *Pseudomonas putida* 5B) or 4.41 mg dry cell weight *E. coli* SW132 wet cells (expressing the active nitrile hydratase from *Comamonas testosteroni* 5-MGAM-4D) in a total volume of 9.664 mL of 0.10 M potassium phosphate buffer (pH 7.0); the amount of dry cell weight present in each reaction was chosen to provide ca. equivalent nitrile hydratase activities (IU/mL) in the reaction mixtures. The final concentration of acrylonitrile was 0.51 M. The mixture was stirred at 25° C. Samples (0.200 mL) of the reaction mixture were mixed with 0.200 mL of 0.200 M sodium butyrate (HPLC standard) in water, and 0.020 mL of 6 N acetic acid. The resulting sample was centrifuged, and the supernatant analyzed by HPLC. The reaction time, % acrylonitrile conversion, and % yield of acrylamide are listed in Table 9. For reactions using *E. coli* SW30 as biocatalyst, a loss of nitrile hydratase activity was observed over the course of the reaction, and incomplete conversion of nitrile was obtained at extended reaction times.

TABLE 9

Comparison of *E. coli* SW30 and *E. coli* SW132 in Acrylonitrile Hydration Reactions

| *E. coli* Construct | mg dcw/mL | time (h) | acrylonitrile conv. (%) | acrylamide yield (%) |
|---|---|---|---|---|
| SW30 | 10.8 | 1.5 | 42 | 38 |
| SW30 | 10.8 | 20 | 80 | 82 |
| SW30 | 10.8 | 45 | 96 | 97 |
| SW132 | 0.44 | 1.5 | 100 | 98 |

Example 15

Comparison of *Comamonas testosteroni* 5-MGAM-4D and *Pseudomonas putida* 5B Nitrile Hydratase for Hydration of 3-Hydroxyvaleronitrile to 3-Hydroxyvaleramide To a 20-mL reaction vessel (equipped with magnetic stirring) was added 3.0 mL of a solution of 0.204 g (2.0 mmol) of 3-hydroxyvaleronitrile in distilled, deionized water and a 1.0 mL suspension of 44 mg dry cell weight of either *E. coli* SW30 wet cells (expressing the active nitrile hydratase from *Pseudomonas putida* 5B) or *E. coli* SW132 wet cells (expressing the active nitrile hydratase from *Comamonas testosteroni* 5-MGAM-4D) in 0.10 M potassium phosphate buffer (pH 7.0). The final concentration of 3-hydroxyvaleronitrile was 0.50 M. The mixture was stirred at 25° C. Samples (0.100 mL) of the reaction mixture were mixed with 0.100 mL of water, 0.200 mL of 0.200 M sodium butyrate (HPLC standard) in water, an 0.020 mL of 6 N HCl. The resulting mixture was centrifuged, and the supernatant analyzed by HPLC. The reaction time, % 3-hydroxyvaleronitrile conversion, and % yield of 3-hydroxyvaleramide are listed in Table 10. For reactions using SW30 as biocatalyst, a loss of nitrile hydratase activity was observed over the course of the reaction, and incomplete conversion of nitrile was obtained at extended reaction times.

TABLE 10

Comparison of *E. coli* SW30 and *E. coli* SW132 in 3-Hydroxyvaleronitrile Reactions

| *E. coli* Construct | mg dcw/mL | Time (h) | 3-hydroxy-valeronitrile conv. (%) | 3-hydroxy-valeramide yield (%) |
|---|---|---|---|---|
| SW30 | 11 | 1 | 12 | 12 |
| SW30 | 11 | 7 | 42 | 40 |
| SW30 | 11 | 24 | 61 | 61 |
| SW132 | 11 | 0.25 | 100 | 100 |

Example 16

Hydration of 3-Hydroxyvaleronitrile to 3-Hydroxyvaleramide by *E. coli* SW137

To a 4-mL reaction vessel (equipped with magnetic stirring) was added 0.75 mL of an aqueous solution containing 0.404 M 3-hydroxyvaleronitrile and 0.25 mL of a suspension of 18 mg dry cell weight *E. coli* SW137 wet cells (prepared as described in Example 6) in 0.10 M potassium phosphate buffer (pH 7.0). The E. coli SW137 cells express the polypeptide having nitrile hydratase activity from *Comamonas testosteroni* 5-MGAM-4D. The final concentration of 3-hydroxyvaleronitrile was 0.303 M. The mixture was stirred at 25° C. Samples (0.100 mL) of the reaction mixture were mixed with 0.100 mL of water, 0.200 mL of 0.200 M sodium butyrate (HPLC standard) in water, an 0.020 mL of 6 N HCl. The resulting mixture was centrifuged, and the supernatant analyzed by HPLC. After 10 min, the conversion of 3-hydroxyvaleronitrile was 100%, and the yield of 3-hydroxyvaleramide was 100%.

Example 17

Immobilization of *Escherichia coli* SW132 Cells in Calcium Cross-Linked Alginate Into a 250-mL media bottle (equipped with magnetic stir bar and containing 59.7 g of distilled, deionized water at 50° C.) was slowly added 3.30 g of FMC BioPolymer Protanal® LF 10/60 alginate with rapid stirring. The mixture was heated to 75–80° C. with rapid stirring until the alginate was completely dissolved, and the resulting solution cooled to 25° C. in a water bath. To the alginate suspension was added 40.8 g of *Escherichia coli* SW132 wet cell paste (22% dry cell weight) and 16.2 mL of distilled water with stirring. The cell/alginate mixture was added dropwise by syringe to 640 mL of 0.20 M calcium acetate buffer (pH 7.0) at 25° C. with stirring. After stirring for 2 h, the buffer was decanted from the resulting beads (82 g), which were resuspended in 200 mL of 0.20 M calcium acetate buffer (pH 7.0) at 25° C. With stirring, 4.10 g of 25 wt % glutaraldehyde (GA) in water was added and the beads mixed for 1.0 h at 25° C. To the suspension was then added 16.4 g of 12.5 wt % polyethylenimine (PEI) (BASF Lupasol® PR971 L, average molecular weight ca. 750,000) in water, and the beads mixed for an additional 1 h at 25° C. The GA/PEI-crosslinked beads were then washed twice with 250 mL of 0.05 M calcium acetate buffer (pH 7.0) at 25° C., and stored in this same buffer at 5° C.

Example 18

Hydration of Nitriles (0.50 M to 3.0 M) to Corresponding Amides by Alginate-Immobilized *Escherichia coli* SW132 Cells in Consecutive Batch Reactions with Biocatalyst Recycle Into a 50-mL jacketed reaction vessel (equipped with an overhead stirrer (temperature-controlled at 25° C. or 35° C.) with a recirculating temperature bath) was placed 4.0 g of GA/PEI-crosslinked *Escherichia coli* SW132 cell/alginate beads prepared as described in Example 17. To the reaction vessel was added 0.2 mL of 0.20 M calcium acetate buffer (pH 7.0, 2.0 mM final calcium ion concentration in reaction mixture), 10, 20, 40 or 60 mmol of acrylonitrile, methacrylonitrile, or 3-hydroxy-valeronitrile, and the final volume of the reaction mixture adjusted to 20 mL by the addition of distilled, deionized water. The mixture was stirred at 25° C. or 35° C. Samples (0.100 mL) of the reaction mixture were mixed with 0.400 mL of water, and then 0.200 mL of the diluted sample was mixed with 0.200 mL of 0.200 M sodium butyrate (acrylonitrile and 3-hydroxyvaleronitrile HPLC external standard) or 0.200 M N-ethylacetamide (methacrylonitrile HPLC external standard) in water. The resulting mixture was centrifuged, and the supernatant analyzed by HPLC.

At the completion of the reaction (100% conversion of nitrile), the product mixture was decanted from the biocatalyst beads, and additional distilled, deionized water, 0.2 mL of 0.20 M calcium acetate buffer (pH 7.0, 2.0 mM final calcium ion concentration in reaction mixture) and 10, 20, 40 or 60 mmol of acrylonitrile, methacrylonitrile, or 3-hydroxy-valeronitrile mixed with the reaction heel (immobilized-cell catalyst and remaining product mixture from the first reaction) at 25° C. or 35° C. At the completion of the second reaction, the product mixture was decanted and a third reaction performed as before. The reaction time, product yield for acrylamide, methacrylamide, or 3-hydroxyvaleramide, and the percent recovered biocatalyst activity for each recycle reaction is listed in Table 11 below.

TABLE 11

Hydration of Nitriles (0.50 M to 3.0 M) to Corresponding Amides by Immobilized E. coli SW132 Cells in Consecutive Batch Reactions with Biocatalyst Recycle

| Nitrile | Conc. (M) | Temp. (° C.) | Rxn # | Time (h) | Amide Yield (%) | Recovered Biocatalyst Activity (%) |
|---|---|---|---|---|---|---|
| Acrylonitrile | 0.53 | 25 | 1 | 0.18 | 100 | 100 |
|  |  |  | 2 | 0.18 | 100 | 94 |
|  |  |  | 3 | 0.12 | 100 | 112 |
| Acrylonitrile | 1.02 | 25 | 1 | 0.25 | 100 | 100 |
|  |  |  | 2 | 0.25 | 100 | 118 |
|  |  |  | 3 | 0.25 | 100 | 124 |
| acrylonitrile | 2.05 | 25 | 1 | 0.5 | 100 | 100 |
|  |  |  | 2 | 0.5 | 100 | 95 |
|  |  |  | 3 | 0.5 | 100 | 100 |
| acrylonitrile | 3.04 | 25 | 1 | 0.75 | 100 | 100 |
|  |  |  | 2 | 0.83 | 100 | 98 |
|  |  |  | 3 | 0.5 | 100 | 106 |
| acrylonitrile | 1.06 | 35 | 1 | 0.15 | 100 | 100 |
|  |  |  | 2 | 0.25 | 100 | 107 |
|  |  |  | 3 | 0.15 | 100 | 110 |
| methacrylonitrile | 1.00 | 25 | 1 | 1.0 | 100 | 100 |
|  |  |  | 2 | 1.0 | 100 | 106 |
|  |  |  | 3 | 1.5 | 99 | 103 |
| 3-hydroxyvaleronitrile | 1.05 | 25 | 1 | 0.75 | 100 | 100 |
|  |  |  | 2 | 0.75 | 100 | 93 |
|  |  |  | 3 | 0.75 | 100 | 84 |
| 3-hydroxyvaleronitrile | 2.05 | 25 | 1 | 1.5 | 100 | 100 |
|  |  |  | 2 | 2.0 | 100 | 102 |
|  |  |  | 3 | 2.0 | 100 | 93 |

Example 19

Immobilization of *E. coli* SW132 Cells in Carrageenan

Into a 250 mL media bottle equipped with magnetic stir bar and containing 54.6 g of water at 50° C. is slowly added 2.88 g of kappa-carrageenan (FMC RG300) with rapid stirring. The mixture is heated to 75–80° C. with rapid stirring until the carrageenan is completely dissolved, and the resulting solution cooled to 55–56° C. (ca. 52° C. gelling temperature) in a thermostated water bath. A suspension of 18.6 g of *E. coli* SW132 wet cell paste (22.0% dry cell wt) in 19.7 g of 0.35 M sodium phosphate buffer (pH 7.3) is heated to 50° C. for 15 min, then added to the carrageenan solution at 55–56° C. with stirring. The cell/carrageenan mixture is immediately added slowly to 383 mL of soybean oil at 50° C. with stirring using an overhead stirrer. After cell/carrageenan droplets of the desired size are produced in the oil by controlling the stirring rate, the temperature of the oil is reduced to 40–42° C. to gel the droplets, and the oil decanted from the resulting beads. The beads are washed with 150 mL of 0.1 M potassium bicarbonate buffer (pH 7.0), then suspended in 182 mL of this same buffer, and 1.9 g of 25 wt % glutaraldehyde in water is added and the beads mixed for 1 h at 25° C. To the mixture is then added 7.6 g of 12.5 wt % polyethylenimine (BASF Lupasol PR971L) average Mw ca. 750,000) in water, and the beads mixed for 1 h at 25° C. The beads are then washed twice with 0.30 M ammonium bicarbonate (pH 7.0), and stored in this same at 5° C.

Example 20

Hydration of Acrylonitrile by Carrageenan-Immobilized *E. coli* SW132 Cells

Into a 50-mL jacketed reaction vessel equipped with an overhead stirrer (temperature-controlled at 35° C. with a recirculating temperature bath) is placed 4.0 g of GA/PEI-crosslinked *E. coli* SW132 cell/carrageenan beads prepared as described in Example 19. To the reaction vessel is then added 1.06 g of acrylonitrile (1.0 M final concentration), the final volume of the reaction mixture adjusted to 20 mL by the addition of distilled, deionized water, and the mixture stirred at 35° C. Samples (0.100 mL) of the reaction mixture are mixed with 0.400 mL of water, and then 0.200 mL of the diluted sample is mixed with 0.200 mL of 0.200 M sodium butyrate (HPLC external standard) in water. The resulting mixture is centrifuged, and the supernatant analyzed by HPLC. At complete conversion of acrylonitrile, there is a quantitative yield of acrylamide.

Example 21

Hydration of Acrylonitrile Using Immobilized Nitrile Hydratase from Partially-Purified Protein Extract of *E. coli* SW132 Cells Into a 25-mL Erlenmeyer flask is weighed 1.0 g of oxirane acrylic beads (Sigma). To the flask is then added ca. 7.5 mL of a solution containing potassium phosphate buffer (50 mM, pH 8.0), and the oxirane acrylic beads suspended in the buffer by briefly mixing the contents of the flask. After cessation of mixing, the beads settle to the bottom of the flask, and the fine particles which float to the top of the mixture are removed by pipette, along with as much of the supernatant which can be removed without disturbing the settled beads. This washing procedure is repeated a second time. To the flask is then added 1.0 mL of the *E. coli* SW132 cell extract supernatant described in Example 12 and the final volume of the mixture adjusted to 10 mL with additional potassium phosphate buffer. The resulting mixture is mixed on a rotary platform shaker for 16 h at 25° C. The mixture is then transferred to a chromatography column equipped with a fritted bed support, and the immobilized nitrile hydratase washed three times with 10 mL of potassium phosphate buffer and stored at 5° C. in this same buffer.

Into a 50-mL jacketed reaction vessel equipped with an overhead stirrer (temperature-controlled at 35° C. with a recirculating temperature bath) is placed 1.0 g of immobilized *E. coli* SW132 nitrile hydratase prepared as described above. To the reaction vessel is then added 1.06 g of acrylonitrile (1.0 M final concentration), the final volume of the reaction mixture adjusted to 20 mL by the addition of distilled, deionized water, and the mixture stirred at 35° C. Samples (0.100 mL) of the reaction mixture are mixed with 0.400 mL of water, and then 0.200 mL of the diluted sample is mixed with 0.200 mL of 0.200 M sodium butyrate (HPLC external standard) in water. The resulting mixture is centrifuged, and the supernatant analyzed by HPLC. At complete conversion of acrylonitrile, there is a quantitative yield of acrylamide.

Example 22

Hydration of 3-Cyanopyridine (0.5 M) to Nicotinamide by Unimmobilized *E. coli* SW132 Cells To a 15-mL polypropylene centrifuge tube was added 3.73 mL of 50 mM potassium phosphate buffer (pH 7.0), 1.0 mL of a suspension of 22.1 mg dry cell weight *E. coli* SW132 wet cells (prepared as described in Example 10) in 50 mM potassium phosphate buffer (pH 7.0), and 0.2660 g of 3-cyanopyridine. The final concentration of 3-cyanopyridine was 0.501 M. The reaction mixture was mixed on a rotating platform at 23° C. After 15 minutes, 7.50 mL of 95:5 acetonitrile/water containing 0.30 M N,N-dimethylbenzamide (HPLC external standard) was added to the reaction, the resulting mixture centrifuged, and a 0.100 mL of the supernatant mixed with 0.900 mL of acetonitrile and analyzed by HPLC. The conversion of 3-cyanopyridine was 100%, and the yields of nicotinamide and nicotinic acid were 100% and 0%, respectively.

Example 23

Hydration of 3-Cyanopyridine (1.0 M) to Nicotinamide by Unimmobilized *E. coli* SW132 Cells To a 15-mL polypropylene centrifuge tube was added 3.47 mL of 50 mM potassium phosphate buffer (pH 7.0), 1.0 mL of a suspension of 55.2 mg dry cell weight *E. coli* SW132 wet cells (prepared as described in Example 10) in 50 mM potassium phosphate buffer (pH 7.0), and 0.5339 g of 3-cyanopyridine. The final concentration of 3-cyanopyridine was 1.00 M. The reaction mixture was mixed on a rotating platform at 23° C. After 30 min, 7.50 mL of 95:5 acetonitrile/water containing 0.30 M N,N-dimethylbenzamide (HPLC external standard) was added to the reaction, the resulting mixture centrifuged, and a 0.100 mL of the supernatant mixed with 0.900 mL of acetonitrile and analyzed by HPLC. The conversion of 3-cyanopyridine was 100%, and the yields of nicotinamide and nicotinic acid were 99% and 0%, respectively.

Example 24

Hydration of 3-Cyanopyridine Using a Partially-Purified Protein Extract of *E. coli* SW132 Cells

*E. coli* SW132 cells (0.5377 g, (prepared as described in Example 10)) were suspended in 5.377 mL of cold breaking buffer consisting of 1 mM DTT and 0.1 mM PMSF in 0.50 mM potassium phosphate buffer (pH 7.0). The suspension (100 mg wet cell weight/mL) was loaded in a French Pressure Mini Cell, and the cells were ruptured at 16000–17000 psi (approximately 110.3–117.2 megapascal (Mpa)). Cell debris was removed from the resulting mixture by centrifugation at 38000 RCF for 15 min. Approximately 4.20 mL of extract supernatant was recovered, having a nitrile hydratase activity equivalent to a 100 mg wet cell weight/mL (22.06 mg dry cell weight/mL) cell suspension.

To a 15-mL polypropylene centrifuge tube was added 3.73 mL of 50 mM potassium phosphate buffer (pH 7.0), 1.0 mL of an *E. coli* SW132 cell extract suspension prepared as described above, and 0.2626 g of 3-cyanopyridine. The final concentration of 3-cyanopyridine was 0.494 M. The reaction mixture was mixed on a rotating platform at 23° C. After 15 min, 7.50 mL of 95:5 acetonitrile/water containing 0.30 M N,N-dimethylbenzamide (HPLC external standard) was added to the reaction, the resulting mixture centrifuged, and a 0.100 mL of the supernatant mixed with 0.900 mL of acetonitrile and analyzed by HPLC. The conversion of 3-cyanopyridine was 100%, and the yields of nicotinamide and nicotinic acid were 100% and 0%, respectively.

Example 25

Hydration of Pyrazinecarbonitrile (0.5 M) to Pyrazinamide by Unimmobilized *E. coli* SW132 Cells To a 15-mL polypropylene centrifuge tube was added 3.73 mL of 50 mM potassium phosphate buffer (pH 7.0), 1.0 mL of a suspension of 22.1 mg dry cell weight *E. coli* SW132 wet cells (prepared as described in Example 10) in 50 mM potassium phosphate buffer (pH 7.0), and 0.2694 g of pyrazinecarbonitrile. The final concentration of pyrazinecarbonitrile was 0.512 M. The reaction mixture was mixed on a rotating platform at 23° C. After 15 min, 7.50 mL of 95:5 acetonitrile/water containing 0.30 M N,N-dimethylbenzamide (HPLC external standard) was added to the reaction, the resulting mixture centrifuged, and a 0.100 mL of the supernatant mixed with 0.900 mL of acetonitrile and analyzed by HPLC. The conversion of pyrazinecarbonitrile was 100%, and the yields of pyrazinamide and pyrazinecarboxylic acid were 100% and 0%, respectively.

Example 26

Hydration of Pyrazinecarbonitrile (1.0 M) to Pyrazinamide by Unimmobilized *E. coli* SW132 Cells To a 15-mL polypropylene centrifuge tube was added 3.47 mL of 50 mM potassium phosphate buffer (pH 7.0), 1.0 mL of a suspension of 55.2 mg dry cell weight *E. coli* SW132 wet cells (prepared as described in Example 10) in 50 mM potassium phosphate buffer (pH 7.0), and 0.5330 g of pyrazinecarbonitrile. The final concentration of pyrazinecarbonitrile was 1.00 M. The reaction mixture was mixed on a rotating platform at 23° C. After 30 min, 7.50 mL of 95:5 acetonitrile/water containing 0.30 M N,N-dimethylbenzamide (HPLC external standard) was added to the reaction, the resulting mixture centrifuged, and a 0.100 mL of the supernatant mixed with 0.900 mL of acetonitrile and analyzed by HPLC. The conversion of pyrazinecarbonitrile was 100%, and the yields of pyrazinamide and pyrazinecarboxylic acid were 100% and 0%, respectively.

Example 27

Hydration of 2-Furancarbonitrile (0.5 M) to 2-Furancarboxamide by Unimmobilized *E. coli* SW132 Cells To a 15-mL polypropylene centrifuge tube was added 3.78 mL of 50 mM potassium phosphate buffer (pH 7.0), 1.0 mL of a suspension of 22.1 mg dry cell weight *E. coli* SW132 wet cells (prepared as described in Example 10) in 50 mM potassium phosphate buffer (pH 7.0), and 0.2381 g of 2-furancarbonitrile. The final concentration of 2-furancarbonitrile was 0.506 M. The reaction mixture was mixed on a rotating platform at 23° C. After 30 min, 7.50 mL of 95:5 acetonitrile/water containing 0.30 M N,N-dimethylbenzamide (HPLC external standard) was added to the reaction, the resulting mixture centrifuged, and a 0.100 mL of the supernatant mixed with 0.900 mL of acetonitrile and analyzed by HPLC. The conversion of 2-furancarbonitrile was 100%, and the yields of 2-furancarboxamide and 2-furancarboxylic acid were 99% and 0%, respectively.

Example 28

Hydration of 2-Thiophenecarbonitrile (0.3 M) to 2-Thiophenecarboxamide by Unimmobilized *E. coli* SW132 Cells To a 15-mL polypropylene centrifuge tube was added 3.86 mL of 50 mM potassium phosphate buffer (pH 7.0), 1.0 mL of a suspension of 22.1 mg dry cell weight *E. coli* SW132 wet cells (prepared as described in Example 10) in 50 mM potassium phosphate buffer (pH 7.0), and 0.1691 g of 2-thiophenecarbonitrile. The final concentration of 2-thiophencarbonitrile was 0.307 M. The reaction mixture was mixed on a rotating platform at 27° C. After 30 min, 7.50 mL of 95:5 acetonitrile/water containing 0.30 M N,N-dimethylbenzamide (HPLC external standard) was added to the reaction, the resulting mixture centrifuged, and a 0.100 mL of the supernatant mixed with 0.900 mL of acetonitrile and analyzed by HPLC. The conversion of 2-thiophenecarbonitrile was 99.5%, and the yields of 2-thiophenecarboxamide and 2-thiophenecarboxylic acid were 98% and 0%, respectively.

Example 29

Hydration of 4-Thiazolecarbonitrile (0.5 M) to 4-Thiazolecarboxamide by Unimmobilized *E. coli* SW132 Cells To a 15-mL polypropylene centrifuge tube is added 3.70 mL of 50 mM potassium phosphate buffer (pH 7.0), 1.0 mL of a suspension of 22.1 mg dry cell weight *E. coli* SW132 wet cells (prepared as described in Example 10) in 50 mM potassium phosphate buffer (pH 7.0), and 0.2754 g of 4-thiazolecarbonitrile. The final concentration of 4-thiazolecarbonitrile is 0.500 M. The reaction mixture is mixed on a rotating platform at 25° C. After 30 min, 7.50 mL of 95:5 acetonitrile/water containing 0.30 M N,N-dimethylbenzamide (HPLC external standard) is added to the reaction, the resulting mixture centrifuged, and a 0.100 mL of the supernatant mixed with 0.900 mL of acetonitrile and analyzed by HPLC. The conversion of 4-thiazolecarbonitrile is 100%, and the yields of 4-thiazolecarboxamide and 4-thiazolecarboxylic acid are 100% and 0%, respectively.

Example 29

Hydration of 3-Cyanopyridine (1.0 M) to Nicotinamide by Alginate-Immobilized *Escherichia coli* SW132 Cells in Consecutive Batch Reactions with Biocatalyst Recycle at 25° C.

Into a 50-mL jacketed reaction vessel (equipped with an overhead stirrer (temperature-controlled at 25° C. with a recirculating temperature bath) was placed 1.0 g of GA/PEI-crosslinked *Escherichia coli* SW132 cell/alginate beads prepared as described in Example 17. To the reaction vessel was added 0.2 mL of 0.20 M calcium acetate buffer (pH 7.0, 2.0 mM final calcium ion concentration in reaction mixture), 16.67 mL of distilled, deionized water, and 2.124 g of 3-cyanopyridine. The final concentration of 3-cyanopyridine was 1.00 M in 20 mL of reaction mixture. Samples (0.100 mL) of the reaction mixture were mixed with 0.400 mL of 95:5 acetonitrile/water containing 0.30 M N,N-dimethylbenzamide (HPLC external standard), and a 0.100 mL of the resulting solution mixed with 0.900 mL of acetonitrile and analyzed by HPLC. After 24 h, the conversion of 3-cyanopyridine was 100%, and the yields of nicotinamide and nicotinic acid were 100% and 0%, respectively. The initial reaction rate for production of nicotinamide, measured during the first 30 min of reaction, was 7.65 mM/minute.

At the completion of the reaction (100% conversion of nitrile), the product mixture was decanted from the biocatalyst beads, and 0.2 mL of 0.20 M calcium acetate buffer (pH 7.0, 2.0 mM final calcium ion concentration in reaction mixture), 16.56 mL of distilled, deionized water, and 2.127 g of 3-cyanopyridine was added to the catalyst beads in the reaction vessel. The final concentration of 3-cyanopyridine was 1.06 M in 20 mL of reaction mixture. Samples (0.100 mL) of the reaction mixture were mixed with 0.400 mL of 95:5 acetonitrile/water containing 0.30 M N,N-dimethylbenzamide (HPLC external standard), and a 0.100 mL of the resulting solution mixed with 0.900 mL of acetonitrile and analyzed by HPLC. After 23 h, the conversion of 3-cyanopyridine was 100%, and the yields of nicotinamide and nicotinic acid were 100% and 0%, respectively. The initial reaction rate for production of nicotinamide, measured during the first 30 min of reaction, was 4.60 mM/minute.

Example 30

Hydration of 3-Cyanopyridine (1.0 M) to Nicotinamide by Alginate-Immobilized *Escherichia coli* SW132 Cells in Consecutive Batch Reactions with Biocatalyst Recycle at 10° C.

Into a 50-mL jacketed reaction vessel (equipped with an overhead stirrer (temperature-controlled at 10° C. with a recirculating temperature bath) was placed 4.0 g of GA/PEI-crosslinked *Escherichia coli* SW132 cell/alginate beads prepared as described in Example 17. To the reaction vessel was added 0.2 mL of 0.20 M calcium acetate buffer (pH 7.0, 2.0 mM final calcium ion concentration in reaction mixture), 13.63 mL of distilled, deionized water, and 2.127 g of 3-cyanopyridine. The final concentration of 3-cyanopyridine was 1.00 M in 20 mL of reaction mixture. Samples (0.100 mL) of the reaction mixture were mixed with 0.400 mL of 95:5 acetonitrile/water containing 0.30 M N,N-dimethylbenzamide (HPLC external standard), and a 0.100 mL of the resulting solution mixed with 0.900 mL of acetonitrile and analyzed by HPLC. After 1 h, the conversion of 3-cyanopyridine was 100%, and the yields of nicotinamide and nicotinic acid were 100% and 0%, respectively. The initial reaction rate for production of nicotinamide, measured during the first 30 min of reaction, was 23.4 mM/minute.

At the completion of the reaction (100% conversion of nitrile), the product mixture was decanted from the biocatalyst beads, and 0.2 mL of 0.20 M calcium acetate buffer (pH 7.0, 2.0 mM final calcium ion concentration in reaction mixture), 13.14 mL of distilled, deionized water, and 2.125 g of 3-cyanopyridine was added to the catalyst beads in the jacketed reaction vessel at 10° C. The final concentration of 3-cyanopyridine was 1.00 M in 20 mL of reaction mixture. Samples (0.100 mL) of the reaction mixture were mixed with 0.400 mL of 95:5 acetonitrile/water containing 0.30 M N,N-dimethylbenzamide (HPLC external standard), and a 0.100 mL of the resulting solution mixed with 0.900 mL of acetonitrile and analyzed by HPLC. After 1 h, the conversion of 3-cyanopyridine was 94%, and the yields of nicotinamide and nicotinic acid were 94% and 0%, respectively. The initial reaction rate for production of nicotinamide, measured during the first 30 min of reaction, was 18.5 mM/minute.

Example 31

Hydration of 3-Cyanopyridine (3.0 M) to Nicotinamide by Alginate-Immobilized *Escherichia coli* SW132 Cells in Consecutive Batch Reactions with Biocatalyst Recycle at 25° C.

Into a 50-mL jacketed reaction vessel (equipped with an overhead stirrer (temperature-controlled at 25° C. with a recirculating temperature bath) was placed 2.0 g of GA/PEI-crosslinked *Escherichia coli* SW132 cell/alginate beads prepared as described in Example 17. To the reaction vessel was added 0.2 mL of 0.20 M calcium acetate buffer (pH 7.0, 2.0 mM final calcium ion concentration in reaction mixture), 11.42 mL of distilled, deionized water, and 6.3648 g of 3-cyanopyridine. The final concentration of 3-cyanopyridine was 3.00 M in 20 mL of reaction mixture. Samples (0.100 mL) of the reaction mixture were mixed with 1.400 mL of 95:5 acetonitrile/water containing 0.30 M N,N-dimethylbenzamide (HPLC external standard), and a 0.100 mL of the resulting solution mixed with 0.900 mL of acetonitrile and analyzed by HPLC. After 48 h, the conversion of 3-cyanopyridine was 100%, and the yields of nicotinamide and nicotinic acid were 100% and 0%, respectively.

What is claimed is:

1. An isolated polynucleotide encoding a polypeptide comprising an amidase, said polypeptide having the amino acid sequence as shown in SEQ ID NO:17.

2. An isolated polynucleotide encoding a polypeptide having amidase activity and having at least 95% identity to the polypeptide from *Comamonas testosteroni* 5-MGAM-4D shown in SEQ ID NO:17.

3. An isolated polynucleotide encoding a polypeptide comprising an amidase enzyme, said isolated polynucleotide having the nucleic acid sequence represented in SEQ ID NO:16.

4. An expression vector comprising any one of the nucleic acid sequences of claims 1–3.

5. A transformed microbial host cell comprising the expression vector of claim 4.

6. The transformed microbial host cell of claim 5 wherein the microbial host cell is a bacterium, yeast, or filamentous fungi.

7. The transformed microbial host cell of claim 6 wherein the microbial host cell is
   a) a bacterium selected from the group consisting of the genera *Escherichia, Pseudomonas, Rhodococcus, Acinectobacter, Bacillus, Methylomonas*, and *Streptomyces;*
   b) a yeast selected from the group consisting of the genera *Pichia, Hansenula*, and *Saccharomyces*; or
   c) a filamentous fungi selected from the group consisting of the genera *Aspergillus, Neurospora*, and *Penicillium*.

8. The transformed microbial host cell of claim 7 wherein the microbial host cell is *Escherichia coli*.

9. A method for producing polypeptides comprising
   a) culturing, under suitable conditions, a transformed microbial host cell containing the expression vector of claim 4; and
   b) recovering the polypeptides produced in step a).

* * * * *

SEQUENCE LISTING

<160> NUMBER OF SEQ ID NOS: 23

<210> SEQ ID NO 1
<211> LENGTH: 633
<212> TYPE: DNA
<213> ORGANISM: Pseudomonas putida 5B

<400> SEQUENCE: 1 atgggcaat cacacacgca tgaccaccat cacgacgggt accaggcacc gcccgaagac    60

-continued

```
atcgcgctgc gggtcaaggc cttggagtct ctgctgatcg agaaaggtct tgtcgaccca      120
gcggccatgg acttggtcgt ccaaacgtat gaacacaagg taggccccg  aaacggcgcc      180 aaagtcgtgg ccaaggcctg gtggaccct  gcctacaagg cccgtctgct ggcagacgca      240
actgcggcaa ttgccgagct gggcttctcc ggggtacagg gcgaggacat ggtcattctg      300
gaaaacaccc ccgccgtcca acgtcttc   gtttgcacct tgtgctcttg ctacccatgg      360
ccgacgctgg gcttgccccc tgcctggtac aaggccgccg cctaccggtc ccgcatggtg      420
agcgacccgc gtgggttct  cgcggagttc ggcctggtga tccccgccaa caaggaaatc      480
cgcgtctggg acaccacggc cgaattgcgc tacatggtgc tgccggaacg gcccggaact      540
gaagcctaca cgaagaaca  actggccgaa ctcgttaccc gcgattcgat gatcggcacc      600
ggcctgccaa cccaacccac cccatctcat taa                                   633
```

<210> SEQ ID NO 2
<211> LENGTH: 654
<212> TYPE: DNA
<213> ORGANISM: Pseudomonas putida 5B

<400> SEQUENCE: 2

```
atgaatggca ttcacgatac tggcggagca catggttatg ggccggttta cagagaaccg       60
aacgaacccg tctttcgcta cgactgggaa aaaacggtca tgtccctgct cccggccctg      120
ctcgccaacg cgaacttcaa cctcgatgaa tttcggcatt cgatcgagcg aatgggcccg      180
gcccactatc tggagggaac ctactacgaa cactggcttc atgtctttga aacctgctg       240 gtcgagaagg gtgtgctcac ggccacggaa gtcgcgaccg gcaaggctgc gtctggcaag      300
acggcgacgc gcgtgctgac gccggccatc gtggacgact cgtcagcacc ggggcttctg      360
cgcccgggag gagggttctc tttttttcct gtgggggaca aggttcgcgt cctcaacaag      420
aacccggtgg ccatacccg  catgccgcgc tacacgcggg caaagtgggg acagtggtca      480
tcgaccatgg tgtgtttcgt gacgccggac accgcggcac acggaaaggg cgagcagccc      540
cagcacgttt acaccgtgag tttcacgtcg gtcgaactgt gggggcaaga cgcttcctcg      600
ccgaaggaca cgattcgcgt cgacttgtgg gatgactacc tggagccagc gtga            654
```

<210> SEQ ID NO 3
<211> LENGTH: 633
<212> TYPE: DNA
<213> ORGANISM: Comamonas testosteroni 5-MGAM-4D
<220> FEATURE:
<221> NAME/KEY: CDS
<222> LOCATION: (1)..(633)

<400> SEQUENCE: 3

```
atg ggg caa tca cac acg cat gac cat cat cac gac ggg tac cag gca        48
Met Gly Gln Ser His Thr His Asp His His His Asp Gly Tyr Gln Ala
1               5                   10                  15 ccg ccc gaa gac atc gcg ctg cgg gtc aag gcc ttg gag tct ctg ctg        96
Pro Pro Glu Asp Ile Ala Leu Arg Val Lys Ala Leu Glu Ser Leu Leu
            20                  25                  30 atc gag aaa ggt ctt gtc gac cca gcg gcc atg gac ttg gtc gtc caa       144
Ile Glu Lys Gly Leu Val Asp Pro Ala Ala Met Asp Leu Val Val Gln
        35                  40                  45 acg tat gaa cac aag gta ggc ccc cga aac ggc gcc aaa gtc gtg gcc       192
Thr Tyr Glu His Lys Val Gly Pro Arg Asn Gly Ala Lys Val Val Ala
    50                  55                  60 aag gcc tgg gtg gac cct gcc tac aag gcc cgt ctg ctg gca gac ggc       240
Lys Ala Trp Val Asp Pro Ala Tyr Lys Ala Arg Leu Leu Ala Asp Gly
```

```
Lys Ala Trp Val Asp Pro Ala Tyr Lys Ala Arg Leu Leu Ala Asp Gly
 65                  70                  75                  80 act gcc ggc att gcc gag ctg ggc ttc tcc ggg gta cag ggc gag gac     288
Thr Ala Gly Ile Ala Glu Leu Gly Phe Ser Gly Val Gln Gly Glu Asp
                 85                  90                  95 atg gtc att ctg gaa aac acc ccc gcc gtc cac aac gtc gtc gtt tgc     336
Met Val Ile Leu Glu Asn Thr Pro Ala Val His Asn Val Val Val Cys
            100                 105                 110 acc ttg tgc tct tgc tac cca tgg ccg acg ctg ggc ttg ccc cct gcc     384
Thr Leu Cys Ser Cys Tyr Pro Trp Pro Thr Leu Gly Leu Pro Pro Ala
        115                 120                 125 tgg tac aag gcc ccg ccc tac cgg tcc cgc atg gtg agc gac ccg cgt     432
Trp Tyr Lys Ala Pro Pro Tyr Arg Ser Arg Met Val Ser Asp Pro Arg
    130                 135                 140 ggg gtt ctc gcg gag ttc ggc ctg gtg atc ccc gcg aag gaa atc cgc     480
Gly Val Leu Ala Glu Phe Gly Leu Val Ile Pro Ala Lys Glu Ile Arg
145                 150                 155                 160 gtc tgg gac acc acg gcc gaa ttg cgc tac atg gtg ctg ccg gaa cgg     528
Val Trp Asp Thr Thr Ala Glu Leu Arg Tyr Met Val Leu Pro Glu Arg
                165                 170                 175 ccc gcg gga act gaa gcc tac agc gaa gaa caa ctg gcc gaa ctc gtt     576
Pro Ala Gly Thr Glu Ala Tyr Ser Glu Glu Gln Leu Ala Glu Leu Val
            180                 185                 190 acc cgc gat tcg atg atc ggc acc ggc ctg ccc atc caa ccc acc cca     624
Thr Arg Asp Ser Met Ile Gly Thr Gly Leu Pro Ile Gln Pro Thr Pro
        195                 200                 205 tct cat taa                                                         633
Ser His
    210

<210> SEQ ID NO 4
<211> LENGTH: 210
<212> TYPE: PRT
<213> ORGANISM: Comamonas testosteroni 5-MGAM-4D

<400> SEQUENCE: 4

Met Gly Gln Ser His Thr His Asp His His Asp Gly Tyr Gln Ala
1               5                   10                  15

Pro Pro Glu Asp Ile Ala Leu Arg Val Lys Ala Leu Glu Ser Leu Leu
            20                  25                  30

Ile Glu Lys Gly Leu Val Asp Pro Ala Ala Met Asp Leu Val Val Gln
        35                  40                  45

Thr Tyr Glu His Lys Val Gly Pro Arg Asn Gly Ala Lys Val Val Ala
    50                  55                  60

Lys Ala Trp Val Asp Pro Ala Tyr Lys Ala Arg Leu Leu Ala Asp Gly
65                  70                  75                  80

Thr Ala Gly Ile Ala Glu Leu Gly Phe Ser Gly Val Gln Gly Glu Asp
                85                  90                  95

Met Val Ile Leu Glu Asn Thr Pro Ala Val His Asn Val Val Val Cys
            100                 105                 110

Thr Leu Cys Ser Cys Tyr Pro Trp Pro Thr Leu Gly Leu Pro Pro Ala
        115                 120                 125

Trp Tyr Lys Ala Pro Pro Tyr Arg Ser Arg Met Val Ser Asp Pro Arg
    130                 135                 140

Gly Val Leu Ala Glu Phe Gly Leu Val Ile Pro Ala Lys Glu Ile Arg
145                 150                 155                 160

Val Trp Asp Thr Thr Ala Glu Leu Arg Tyr Met Val Leu Pro Glu Arg
                165                 170                 175
```

```
Pro Ala Gly Thr Glu Ala Tyr Ser Glu Glu Gln Leu Ala Glu Leu Val
            180                 185                 190

Thr Arg Asp Ser Met Ile Gly Thr Gly Leu Pro Ile Gln Pro Thr Pro
        195                 200                 205

Ser His
    210

<210> SEQ ID NO 5
<211> LENGTH: 657
<212> TYPE: DNA
<213> ORGANISM: Comamonas testosteroni 5-MGAM-4D
<220> FEATURE:
<221> NAME/KEY: CDS
<222> LOCATION: (1)..(657)

<400> SEQUENCE: 5 atg aat ggc att cac gat act ggg gga gca cat ggt tat ggg ccg gtt       48
Met Asn Gly Ile His Asp Thr Gly Gly Ala His Gly Tyr Gly Pro Val
1               5                   10                  15 tac aga gaa ccg aac gaa ccc gtc ttt cgc tac gac tgg gaa aaa acg       96
Tyr Arg Glu Pro Asn Glu Pro Val Phe Arg Tyr Asp Trp Glu Lys Thr
                20                  25                  30 gtc atg tcc ctg ttc ccg gcg ctg ttc gcc aac ggc aac ttc aac ctc      144
Val Met Ser Leu Phe Pro Ala Leu Phe Ala Asn Gly Asn Phe Asn Leu
            35                  40                  45 gat gag ttt cga cac ggc atc gag cgc atg aac ccc atc gac tac ctg      192
Asp Glu Phe Arg His Gly Ile Glu Arg Met Asn Pro Ile Asp Tyr Leu
        50                  55                  60 aag gga acc tac tac gaa cac tgg atc cat tcc atc gaa acc ttg ctg      240
Lys Gly Thr Tyr Tyr Glu His Trp Ile His Ser Ile Glu Thr Leu Leu
65                  70                  75                  80 gtc gaa aag ggt gtg ctc acg gca acg gaa ctc gcg acc ggc aag gca      288
Val Glu Lys Gly Val Leu Thr Ala Thr Glu Leu Ala Thr Gly Lys Ala
                85                  90                  95 tct ggc aag aca gcg aca ccg gtg ctg acg ccg gcc atc gtg gac gga      336
Ser Gly Lys Thr Ala Thr Pro Val Leu Thr Pro Ala Ile Val Asp Gly
            100                 105                 110 ctg ctc agc acc ggg gct tct gcc gcc cgg gag gag ggt gcg cgg gcg      384
Leu Leu Ser Thr Gly Ala Ser Ala Ala Arg Glu Glu Gly Ala Arg Ala
        115                 120                 125 cgg ttc gct gtg ggg gac aag gtt cgc gtc ctc aac aag aac ccg gtg      432
Arg Phe Ala Val Gly Asp Lys Val Arg Val Leu Asn Lys Asn Pro Val
    130                 135                 140 ggc cat acc cgc atg ccg cgc tac acg cgg ggc aaa gtg ggg aca gtg      480
Gly His Thr Arg Met Pro Arg Tyr Thr Arg Gly Lys Val Gly Thr Val
145                 150                 155                 160 gtc atc gac cat ggt gtg ttc gtg acg ccg gac acc gcg gca cac gga      528
Val Ile Asp His Gly Val Phe Val Thr Pro Asp Thr Ala Ala His Gly
                165                 170                 175 aag ggc gag cac ccc cag cac gtt tac acc gtg agt ttc acg tcg gtc      576
Lys Gly Glu His Pro Gln His Val Tyr Thr Val Ser Phe Thr Ser Val
            180                 185                 190 gaa ctg tgg ggg caa gac gcc tcc tcg ccg aag gac acg att cgc gtc      624
Glu Leu Trp Gly Gln Asp Ala Ser Ser Pro Lys Asp Thr Ile Arg Val
        195                 200                 205 gac ttg tgg gat gac tac ctg gag cca gcg tga                          657
Asp Leu Trp Asp Asp Tyr Leu Glu Pro Ala
    210                 215

<210> SEQ ID NO 6
```

<211> LENGTH: 218
<212> TYPE: PRT
<213> ORGANISM: Comamonas testosteroni 5-MGAM-4D

<400> SEQUENCE: 6

```
Met Asn Gly Ile His Asp Thr Gly Gly Ala His Gly Tyr Gly Pro Val
  1               5                  10                  15
Tyr Arg Glu Pro Asn Glu Pro Val Phe Arg Tyr Asp Trp Glu Lys Thr
             20                  25                  30
Val Met Ser Leu Phe Pro Ala Leu Phe Ala Asn Gly Asn Phe Asn Leu
         35                  40                  45
Asp Glu Phe Arg His Gly Ile Glu Arg Met Asn Pro Ile Asp Tyr Leu
     50                  55                  60
Lys Gly Thr Tyr Tyr Glu His Trp Ile His Ser Ile Glu Thr Leu Leu
 65                  70                  75                  80
Val Glu Lys Gly Val Leu Thr Ala Thr Glu Leu Ala Thr Gly Lys Ala
                 85                  90                  95
Ser Gly Lys Thr Ala Thr Pro Val Leu Thr Pro Ala Ile Val Asp Gly
            100                 105                 110
Leu Leu Ser Thr Gly Ala Ser Ala Ala Arg Glu Glu Gly Ala Arg Ala
        115                 120                 125
Arg Phe Ala Val Gly Asp Lys Val Arg Val Leu Asn Lys Asn Pro Val
    130                 135                 140
Gly His Thr Arg Met Pro Arg Tyr Thr Arg Gly Lys Val Gly Thr Val
145                 150                 155                 160
Val Ile Asp His Gly Val Phe Val Thr Pro Asp Thr Ala Ala His Gly
                165                 170                 175
Lys Gly Glu His Pro Gln His Val Tyr Thr Val Ser Phe Thr Ser Val
            180                 185                 190
Glu Leu Trp Gly Gln Asp Ala Ser Ser Pro Lys Asp Thr Ile Arg Val
        195                 200                 205
Asp Leu Trp Asp Asp Tyr Leu Glu Pro Ala
    210                 215
```

<210> SEQ ID NO 7
<211> LENGTH: 1386
<212> TYPE: DNA
<213> ORGANISM: Comamonas testosteroni 5-MGAM-4D

<400> SEQUENCE: 7

```
tcgatgccga gttgaagtcg ctgtacccct tttttcaacc acaccaggag aaccgcacca      60
tggggcaatc acacacgcat gaccaccatc acgacgggta ccaggcaccg cccgaagaca     120
tcgcgctgcg ggtcaaggcc ttggagtctc tgctgatcga gaaaggtctt gtcgacccag     180
cggccatgga cttggtcgtc caaacgtatg aacacaaggt aggccccga acggcgcca      240
aagtcgtggc caaggcctgg gtggaccctg cctacaaggc ccgtctgctg cagacggca      300
ctgccggcat tgccgagctg ggcttctccg gggtacaggg cgaggacatg gtcattctgg     360
aaaacacccc cgccgtccac aacgtcgtcg tttgcacctt gtgctcttgc tacccatggc     420
cgacgctggg cttgcccct gcctggtaca aggccccgcc ctaccggtcc gcatggtga      480
gcgacccgcg tggggttctc gcggagttcg gcctggtgat cccgcgaag gaaatccgcg     540
tctgggacac cacggccgaa ttgcgctaca tggtgctgcc ggaacggccc gcgggaactg     600
aagcctacag cgaagaacaa ctggccgaac tcgttacccg cgattcgatg atcggcaccg     660
gcctgcccat ccaacccacc ccatctcatt aaggagttcg tcatgaatgg cattcacgat     720
```

```
actgggggag cacatggtta tgggccggtt tacagagaac cgaacgaacc cgtctttcgc      780
tacgactggg aaaaaacggt catgtccctg ttcccggcgc tgttcgccaa cggcaacttc      840
aacctcgatg agtttcgaca cggcatcgag cgcatgaacc ccatcgacta cctgaaggga      900
acctactacg aacactggat ccattccatc gaaaccttgc tggtcgaaaa gggtgtgctc      960
acggcaacgg aactcgcgac cggcaaggca tctggcaaga cagcgacacc ggtgctgacg     1020
ccggccatcg tggacggact gctcagcacc ggggcttctg ccgcccggga ggagggtgcg     1080
cgggcgcggt tcgctgtggg ggacaaggtt cgcgtcctca acaagaaccc ggtgggccat     1140
acccgcatgc gcgcgctaca cgcggggcaaa gtggggacag tggtcatcga ccatggtgtg     1200
ttcgtgacgc cggacaccgc ggcacacgga aagggcgagc accccagca cgtttacacc      1260 gtgagtttca cgtcggtcga actgtggggg caagacgcct cctcgccgaa ggacacgatt     1320
cgcgtcgact tgtgggatga ctacctggag ccagcgtgat catgaaagac gaacggtttc     1380
cattgc                                                                 1386
```

<210> SEQ ID NO 8
<211> LENGTH: 23
<212> TYPE: DNA
<213> ORGANISM: artificial sequence
<220> FEATURE:
<223> OTHER INFORMATION: Primer 1

<400> SEQUENCE: 8

```
tcgatgccga gttgaagtcg ctg                                                23
```

<210> SEQ ID NO 9
<211> LENGTH: 23
<212> TYPE: DNA
<213> ORGANISM: artificial sequence
<220> FEATURE:
<223> OTHER INFORMATION: Primer 2

<400> SEQUENCE: 9

```
gcaatggaaa ccgttcgtct ttc                                                23
```

<210> SEQ ID NO 10
<211> LENGTH: 923
<212> TYPE: DNA
<213> ORGANISM: Comamonas testosteroni 5-MGAM-4D

<400> SEQUENCE: 10

```
tcatgaaaga cgaacggttt ccattgccag agggttcgct gaaggacctc gatggccctg        60
tgtttgacga gccttggcag tcccaggcgt ttgccttggt ggtcagcatg cacaaggccg       120
gtctctttca gtggaaagac tgggccgaga ccttcaccgc cgaaatcgac gcttccccgg       180
ctctgcccgg cgaaagcgtc aacgacacct actaccggca atgggtgtcg gcgctggaaa      240
agttggtggc gtcgctgggg cttgtgacgg gtggagacgt caactcgcgc gcacaggagt      300
ggaaacaggc ccacctcaac accccacatg ggcacccgat cctgctggcc catgcgcttt      360
gcccgccagc gatcgacccc aagcacaagc acgagccaaa acgctcaccg atcaaggtcg      420
ttgccgcaat ggcttgagat ccactgtcct gtttccctac cttgaatgga gtaaaccatg      480
agttcatttt ctaccactgc cgtccccgcc gcccagcgcc tgagcgccac gcgcagctta      540
ctgttgcaac tgtccgctgg cgccgcgctg ggcctggtcg tcctgtacgg cgtggctttt      600
gccgaaagcc cgcttgcgca caacgccgcg cacgatgttc gccacgtgac ggtcaagcct      660
```

-continued

| | |
|---|---|
| tgtcactaac tgtggcccac ccccgccgcg ctgcgcgcga cccctccag ggggcaaacc | 720 |
| gagtggcccg gcggagccgg ttccaccgcg ttcccggtgg ggtgcactgc tggcgttgcg | 780 |
| ggtcttgttt cggctggatg gtttcttgac ggagccacac cgtcgctcat ctgtatatgg | 840 |
| agagggtcat gatttttcga cgcttgatct gggcggcgct ggccgtggcc ttgctggtgg | 900 |
| gcagtttgca gtcgggtctg cag | 923 |

<210> SEQ ID NO 11
<211> LENGTH: 2223
<212> TYPE: DNA
<213> ORGANISM: Comamonas testosteroni 5-MGAM-4D

<400> SEQUENCE: 11

| | |
|---|---|
| atggggcaat cacacacgca tgaccaccat cacgacgggt accaggcacc gcccgaagac | 60 |
| atcgcgctgc gggtcaaggc cttggagtct ctgctgatcg agaaaggtct tgtcgaccca | 120 |
| gcggccatgg acttggtcgt ccaaacgtat gaacacaagg taggccccg aaacggcgcc | 180 |
| aaagtcgtgg ccaaggcctg ggtggaccct gcctacaagg cccgtctgct ggcagacggc | 240 |
| actgccggca ttgccgagct gggcttctcc ggggtacagg gcgaggacat ggtcattctg | 300 |
| gaaaacaccc ccgccgtcca acgtcgtc gtttgcacct tgtgctcttg ctacccatgg | 360 |
| ccgacgctgg gcttgccccc tgcctggtac aaggccccgc cctaccggtc cgcatggtg | 420 |
| agcgacccgc gtggggttct cgcggagttc ggcctggtga tccccgcgaa ggaaatccgc | 480 |
| gtctgggaca ccacgccga attgcgctac atggtgctgc cggaacggcc cgcgggaact | 540 |
| gaagcctaca gcgaagaaca actggccgaa ctcgttaccc gcgattcgat gatcggcacc | 600 |
| ggcctgccca tccaacccac cccatctcat taaggagttc gtcatgaatg cattcacga | 660 |
| tactggggga gcacatggtt atgggccggt ttacagaaa ccgaacgaac ccgtctttcg | 720 |
| ctacgactgg gaaaaaacgg tcatgtccct gttcccggcg ctgttcgcca acggcaactt | 780 |
| caacctcgat gagtttcgac acggcatcga gcgcatgaac cccatcgact acctgaaggg | 840 |
| aacctactac gaacactgga tccattccat cgaaaccttg ctggtcgaaa agggtgtgct | 900 |
| cacggcaacg gaactcgcga ccggcaaggc atctggcaag acagcgacac cggtgctgac | 960 |
| gccggccatc gtggacggac tgctcagcac cggggcttct gccgcccggg aggagggtgc | 1020 |
| gcgggcgcgg ttcgctgtgg gggacaaggt tcgcgtcctc aacaagaacc cggtgggcca | 1080 |
| tacccgcatg ccgcgctaca cgcgggcaa agtggggaca gtggtcatcg accatggtgt | 1140 |
| gttcgtgacg ccggacaccg cggcacacgg aaagggcgag cacccccagc acgtttacac | 1200 |
| cgtgagtttc acgtcggtcg aactgtgggg gcaagacgcc tcctcgccga aggacacgat | 1260 |
| tcgcgtcgac ttgtgggatg actacctgga gccagcgtga tcatgaaaga cgaacggttt | 1320 |
| ccattgccag agggttcgct gaaggacctc gatggccctg tgtttgacga gccttggcag | 1380 |
| tcccaggcgt ttgccttggt ggtcagcatg acaaggccg gtctctttca gtggaaagac | 1440 |
| tgggccgaga ccttcaccgc cgaaatcgac gcttccccgg ctctgcccgg cgaaagcgtc | 1500 |
| aacgacacct actaccggca atgggtgtcg gcgctggaaa agttggtggc gtcgctgggg | 1560 |
| cttgtgacgg gtggagacgt caactcgcgc gcacaggagt ggaaacaggc ccacctcaac | 1620 |
| accccacatg ggcacccgat cctgctggcc catgcgcttt gccgccagc gatcgacccc | 1680 |
| aagcacaagc acgagccaaa acgctcaccg atcaaggtcg ttgccgcaat ggcttgagat | 1740 |
| ccactgtcct gtttccctac cttgaatgga gtaaaccatg agttcatttt ctaccactgc | 1800 |
| cgtccccgcc gcccagcgcc tgagcgccac gcgcagctta ctgttgcaac tgtccgctgg | 1860 |

```
cgccgcgctg ggcctggtcg tcctgtacgg cgtggctttt gccgaaagcc cgcttgcgca    1920
caacgccgcg cacgatgttc gccacgtgac ggtcaagcct tgtcactaac tgtggcccac    1980
ccccgccgcg ctgcgcgcga ccccctccag ggggcaaacc gagtggcccg gcggagccgg    2040
ttccaccgcg ttcccggtgg ggtgcactgc tggcgttgcg ggtcttgttt cggctggatg    2100
gtttcttgac ggagccacac cgtcgctcat ctgtatatgg agagggtcat gattttcga     2160 cgcttgatct gggcggcgct ggccgtggcc ttgctggtgg gcagtttgca gtcgggtctg    2220
cag                                                                  2223
```

```
<210> SEQ ID NO 12
<211> LENGTH: 30
<212> TYPE: DNA
<213> ORGANISM: artificial sequence
<220> FEATURE:
<223> OTHER INFORMATION: Primer 3

<400> SEQUENCE: 12
ctgaagcttc aaggtaggga aacaggacag                                      30

<210> SEQ ID NO 13
<211> LENGTH: 216
<212> TYPE: DNA
<213> ORGANISM: Comamonas testosteroni 5-MGAM-4D
<220> FEATURE:
<221> NAME/KEY: CDS
<222> LOCATION: (1)..(216)

<400> SEQUENCE: 13 atg gcc ctg tgt ttg acg agc ctt ggc agt ccc agg cgt ttg cct tgg     48
Met Ala Leu Cys Leu Thr Ser Leu Gly Ser Pro Arg Arg Leu Pro Trp
1               5                   10                  15 tgg tca gca tgc aca agg ccg gtc tct ttc agt gga aag act ggg ccg     96
Trp Ser Ala Cys Thr Arg Pro Val Ser Phe Ser Gly Lys Thr Gly Pro
            20                  25                  30 aga cct tca ccg ccg aaa tcg acg ctt ccc cgg ctc tgc ccg gcg aaa    144
Arg Pro Ser Pro Pro Lys Ser Thr Leu Pro Arg Leu Cys Pro Ala Lys
        35                  40                  45 gcg tca acg aca cct act acc ggc aat ggg tgt cgg cgc tgg aaa agt    192
Ala Ser Thr Thr Pro Thr Thr Gly Asn Gly Cys Arg Arg Trp Lys Ser
    50                  55                  60 tgg tgg cgt cgc tgg ggc ttg tga                                     216
Trp Trp Arg Arg Trp Gly Leu
65                  70

<210> SEQ ID NO 14
<211> LENGTH: 71
<212> TYPE: PRT
<213> ORGANISM: Comamonas testosteroni 5-MGAM-4D

<400> SEQUENCE: 14

Met Ala Leu Cys Leu Thr Ser Leu Gly Ser Pro Arg Arg Leu Pro Trp
1               5                   10                  15

Trp Ser Ala Cys Thr Arg Pro Val Ser Phe Ser Gly Lys Thr Gly Pro
            20                  25                  30

Arg Pro Ser Pro Pro Lys Ser Thr Leu Pro Arg Leu Cys Pro Ala Lys
        35                  40                  45

Ala Ser Thr Thr Pro Thr Thr Gly Asn Gly Cys Arg Arg Trp Lys Ser
    50                  55                  60

Trp Trp Arg Arg Trp Gly Leu
```

<210> SEQ ID NO 15
<211> LENGTH: 669
<212> TYPE: DNA
<213> ORGANISM: Comamonas testosteroni 5-MGAM-4D

<400> SEQUENCE: 15

| | | |
|---|---|---|
| gaattcgcct atggcgtcat cactccgaag tcgcgcaacc cctgggaccc gggaagaaca | 60 |
| ccgggtggct ccagcggcgg ctcggcggcc acggtcgcag cctgcggcgt ctacttggcg | 120 |
| accggcaccg acaccggtgg atccgttcgc atcccttcgt cgatgtgcaa caccgtaggc | 180 |
| ctgaagccaa cctacgggcg cgtgagccgt gccggtgtga gttcactttc ctggagcctg | 240 |
| gaccatccag gcccgatcac gcgcaccgtg aagacacgg cgctcagcct tcaggtgatg | 300 |
| gctggcttcg atccagccga ccgcggctcg ttggatgagc cggtgcccag ctatgccgaa | 360 |
| gggctcggcc aaggcgtgaa aggcctgcgc gtgggcgtgc cgaagaacta cttcttcgac | 420 |
| cgcgtggacc cggaagttga agtgcggtt cgtgccgcca tcgatcaact gaaagagctg | 480 |
| ggcgccgaac tggtggaagt cgaagtgccc atggccgagc agatcatccc ggtggagttc | 540 |
| gggatcgtgc tacccgaagc cagcgcctac caccgcacga tgctgcgcga gtcacccgag | 600 |
| ctctacaccg ccgatgtccg catactgctg gaactcggaa atctagtcac cgccaccgac | 660 |
| tacctgcag | 669 |

<210> SEQ ID NO 16
<211> LENGTH: 1407
<212> TYPE: DNA
<213> ORGANISM: Comamonas testosteroni 5-MGAM-4D
<220> FEATURE:
<221> NAME/KEY: CDS
<222> LOCATION: (1)..(1407)

<400> SEQUENCE: 16

| | |
|---|---|
| atg agt tcg cta acc cgc ctc acc ctc gcg caa gtt gcg cag aaa ctt<br>Met Ser Ser Leu Thr Arg Leu Thr Leu Ala Gln Val Ala Gln Lys Leu<br>1               5                  10                  15 | 48 |
| aag gca cgg gaa gtc tcc gcc gtt gaa gtt ctg gac gcc tgt ctg acg<br>Lys Ala Arg Glu Val Ser Ala Val Glu Val Leu Asp Ala Cys Leu Thr<br>            20                  25                  30 | 96 |
| cag gtg cgc tcc acc gaa aaa cag atc agt gcg tac gtg tgc gtg ctg<br>Gln Val Arg Ser Thr Glu Lys Gln Ile Ser Ala Tyr Val Cys Val Leu<br>        35                  40                  45 | 144 |
| gag gat cag gcc cgt gca gca gcc cag caa gct gac gcc gac atc agc<br>Glu Asp Gln Ala Arg Ala Ala Gln Gln Ala Asp Ala Asp Ile Ser<br>    50                  55                  60 | 192 |
| gcc ggg cgc tgg aaa ggc ccg ctg cat ggc gtg cct gta gcg gtc aag<br>Ala Gly Arg Trp Lys Gly Pro Leu His Gly Val Pro Val Ala Val Lys<br>65                  70                  75                  80 | 240 |
| gac tta tac gac atc gct ggc gta ccc acc acg gca tcg tcg cgc cag<br>Asp Leu Tyr Asp Ile Ala Gly Val Pro Thr Thr Ala Ser Ser Arg Gln<br>                85                  90                  95 | 288 |
| cgc acg aat tgg acg ccg cag caa gac tgc gcc gta gtc cgg cgc ttg<br>Arg Thr Asn Trp Thr Pro Gln Gln Asp Cys Ala Val Val Arg Arg Leu<br>            100                 105                 110 | 336 |
| aaa gac gca ggt gcc gtt atc ctt ggc aag acc cat acg cac gaa ttc<br>Lys Asp Ala Gly Ala Val Ile Leu Gly Lys Thr His Thr His Glu Phe<br>        115                 120                 125 | 384 |
| gcc tat ggc gtc atc act ccg aag tcg cgc aac ccc tgg gac ccg gga<br>Ala Tyr Gly Val Ile Thr Pro Lys Ser Arg Asn Pro Trp Asp Pro Gly | 432 |

-continued

```
              130                 135                 140
aga aca ccg ggt ggc tcc agc ggc ggc tcg gcg gcc acg gtc gca gcc      480
Arg Thr Pro Gly Gly Ser Ser Gly Gly Ser Ala Ala Thr Val Ala Ala
145                 150                 155                 160 tgc ggc gtc tac ttg gcg acc ggc acc gac acc ggt gga tcc gtt cgc      528
Cys Gly Val Tyr Leu Ala Thr Gly Thr Asp Thr Gly Gly Ser Val Arg
                165                 170                 175 atc cct tcg tcg atg tgc aac acc gta ggc ctg aag cca acc tac ggg      576
Ile Pro Ser Ser Met Cys Asn Thr Val Gly Leu Lys Pro Thr Tyr Gly
            180                 185                 190 cgc gtg agc cgt gcc ggt gtg agt tca ctt tcc tgg agc ctg gac cat      624
Arg Val Ser Arg Ala Gly Val Ser Ser Leu Ser Trp Ser Leu Asp His
        195                 200                 205 cca ggc ccg atc acg cgc acc gtg gaa gac acg gcg ctc agc ctt cag      672
Pro Gly Pro Ile Thr Arg Thr Val Glu Asp Thr Ala Leu Ser Leu Gln
    210                 215                 220 gtg atg gct ggc ttc gat cca gcc gac cgc ggc tcg ttg gat gag ccg      720
Val Met Ala Gly Phe Asp Pro Ala Asp Arg Gly Ser Leu Asp Glu Pro
225                 230                 235                 240 gtg ccc agc tat gcc gaa ggg ctc ggc caa ggc gtg aaa ggc ctg cgc      768
Val Pro Ser Tyr Ala Glu Gly Leu Gly Gln Gly Val Lys Gly Leu Arg
                245                 250                 255 gtg ggc gtg ccg aag aac tac ttc ttc gac cgc gtg gac ccg gaa gtt      816
Val Gly Val Pro Lys Asn Tyr Phe Phe Asp Arg Val Asp Pro Glu Val
            260                 265                 270 gaa agt gcg gtt cgt gcc gcc atc gat caa ctg aaa gag ctg ggc gcc      864
Glu Ser Ala Val Arg Ala Ala Ile Asp Gln Leu Lys Glu Leu Gly Ala
        275                 280                 285 gaa ctg gtg gaa gtc gaa gtg ccc atg gcc gag cag atc atc ccg gtg      912
Glu Leu Val Glu Val Glu Val Pro Met Ala Glu Gln Ile Ile Pro Val
    290                 295                 300 gag ttc ggg atc gtg cta ccc gaa gcc agc gcc tac cac cgc acg atg      960
Glu Phe Gly Ile Val Leu Pro Glu Ala Ser Ala Tyr His Arg Thr Met
305                 310                 315                 320 ctg cgc gag tca ccc gag ctc tac acc gcc gat gtc cgc ata ctg ctg     1008
Leu Arg Glu Ser Pro Glu Leu Tyr Thr Ala Asp Val Arg Ile Leu Leu
                325                 330                 335 gaa ctc gga aat cta gtc acc gcc acc gac tac ctg cag gcg cag cgc     1056
Glu Leu Gly Asn Leu Val Thr Ala Thr Asp Tyr Leu Gln Ala Gln Arg
            340                 345                 350 gtc cgt acg ctg atg cag cgc gcg gtg gcc gag atg ttc cag cgc atc     1104
Val Arg Thr Leu Met Gln Arg Ala Val Ala Glu Met Phe Gln Arg Ile
        355                 360                 365 gat gtg ctg atc gca ccc aca ctg ccc atc ccg gct gct cgc agc ggg     1152
Asp Val Leu Ile Ala Pro Thr Leu Pro Ile Pro Ala Ala Arg Ser Gly
    370                 375                 380 gag gag gtc cac aca tgg ccg gac ggc acg gta gag gcg ttg ttc atg     1200
Glu Glu Val His Thr Trp Pro Asp Gly Thr Val Glu Ala Leu Phe Met
385                 390                 395                 400 gcc tat acg cgc ttc acc tcg ttc ggc aac gtg aca gga tta ccc acg     1248
Ala Tyr Thr Arg Phe Thr Ser Phe Gly Asn Val Thr Gly Leu Pro Thr
                405                 410                 415 ctg aac ctg ccc tgt ggt ttc tcc aag gat ggg ttg ccg atc ggc atg     1296
Leu Asn Leu Pro Cys Gly Phe Ser Lys Asp Gly Leu Pro Ile Gly Met
            420                 425                 430 cag atc acc ggc cgg ccg ctg gac gag aag acc ctg ctg cgt gct ggg     1344
Gln Ile Thr Gly Arg Pro Leu Asp Glu Lys Thr Leu Leu Arg Ala Gly
        435                 440                 445 ctg gcc tac gag aaa gcc acg acc tgg cac cag cgt cat ccg gaa ctg     1392
```

```
            Leu Ala Tyr Glu Lys Ala Thr Thr Trp His Gln Arg His Pro Glu Leu
                450                 455                 460 atc gga gcg ggc tga                                                      1407
Ile Gly Ala Gly
465
```

<210> SEQ ID NO 17
<211> LENGTH: 468
<212> TYPE: PRT
<213> ORGANISM: Comamonas testosteroni 5-MGAM-4D

<400> SEQUENCE: 17

```
Met Ser Ser Leu Thr Arg Leu Thr Leu Ala Gln Val Ala Gln Lys Leu
1               5                  10                  15

Lys Ala Arg Glu Val Ser Ala Val Glu Val Leu Asp Ala Cys Leu Thr
                20                  25                  30

Gln Val Arg Ser Thr Glu Lys Gln Ile Ser Ala Tyr Val Cys Val Leu
            35                  40                  45

Glu Asp Gln Ala Arg Ala Ala Ala Gln Gln Ala Asp Ala Asp Ile Ser
    50                  55                  60

Ala Gly Arg Trp Lys Gly Pro Leu His Gly Val Pro Val Ala Val Lys
65                  70                  75                  80

Asp Leu Tyr Asp Ile Ala Gly Val Pro Thr Thr Ala Ser Ser Arg Gln
                85                  90                  95

Arg Thr Asn Trp Thr Pro Gln Gln Asp Cys Ala Val Val Arg Arg Leu
            100                 105                 110

Lys Asp Ala Gly Ala Val Ile Leu Gly Lys Thr His Thr His Glu Phe
        115                 120                 125

Ala Tyr Gly Val Ile Thr Pro Lys Ser Arg Asn Pro Trp Asp Pro Gly
    130                 135                 140

Arg Thr Pro Gly Gly Ser Ser Gly Gly Ser Ala Ala Thr Val Ala Ala
145                 150                 155                 160

Cys Gly Val Tyr Leu Ala Thr Gly Thr Asp Thr Gly Gly Ser Val Arg
                165                 170                 175

Ile Pro Ser Ser Met Cys Asn Thr Val Gly Leu Lys Pro Thr Tyr Gly
            180                 185                 190

Arg Val Ser Arg Ala Gly Val Ser Ser Leu Ser Trp Ser Leu Asp His
        195                 200                 205

Pro Gly Pro Ile Thr Arg Thr Val Glu Asp Thr Ala Leu Ser Leu Gln
    210                 215                 220

Val Met Ala Gly Phe Asp Pro Ala Asp Arg Gly Ser Leu Asp Glu Pro
225                 230                 235                 240

Val Pro Ser Tyr Ala Glu Gly Leu Gly Gln Gly Val Lys Gly Leu Arg
                245                 250                 255

Val Gly Val Pro Lys Asn Tyr Phe Phe Asp Arg Val Asp Pro Glu Val
            260                 265                 270

Glu Ser Ala Val Arg Ala Ala Ile Asp Gln Leu Lys Glu Leu Gly Ala
        275                 280                 285

Glu Leu Val Glu Val Glu Val Pro Met Ala Glu Gln Ile Ile Pro Val
    290                 295                 300

Glu Phe Gly Ile Val Leu Pro Glu Ala Ser Ala Tyr His Arg Thr Met
305                 310                 315                 320

Leu Arg Glu Ser Pro Glu Leu Tyr Thr Ala Asp Val Arg Ile Leu Leu
                325                 330                 335

Glu Leu Gly Asn Leu Val Thr Ala Thr Asp Tyr Leu Gln Ala Gln Arg
```

```
                    340             345             350
Val Arg Thr Leu Met Gln Arg Ala Val Ala Glu Met Phe Gln Arg Ile
        355                 360                 365

Asp Val Leu Ile Ala Pro Thr Leu Pro Ile Pro Ala Ala Arg Ser Gly
        370                 375                 380

Glu Glu Val His Thr Trp Pro Asp Gly Thr Val Glu Ala Leu Phe Met
385                 390                 395                 400

Ala Tyr Thr Arg Phe Thr Ser Phe Gly Asn Val Thr Gly Leu Pro Thr
                405                 410                 415

Leu Asn Leu Pro Cys Gly Phe Ser Lys Asp Gly Leu Pro Ile Gly Met
        420                 425                 430

Gln Ile Thr Gly Arg Pro Leu Asp Glu Lys Thr Leu Leu Arg Ala Gly
        435                 440                 445

Leu Ala Tyr Glu Lys Ala Thr Thr Trp His Gln Arg His Pro Glu Leu
        450                 455                 460

Ile Gly Ala Gly
465

<210> SEQ ID NO 18
<211> LENGTH: 7415
<212> TYPE: DNA
<213> ORGANISM: Comamonas testosteroni 5-MGAM-4D

<400> SEQUENCE: 18
ctgcagagtg catggcatcg agctggcggg cgctccagct gctggggttg cgccgcatgc      60
cccacagcag ctgcctgagc gtcttgcggc cgccagcgcc cagcgcggct cgcaccgcct     120
gcgcgtcggt ggccatctcc gcgcggcgca cctggtccat cgcctcgatg ccatcgaga      180
cgacgtgaaa gcggtcgtag ctgatctgcg cctcgggcag cgccagcgcc acgcccttgg     240
cgtaggctgc gctcatgtcc atgcacacgt gccgcacctg gcgggatcg ccgccatggg      300
ccttcagatc ctcggcgaac tccaccaccg tgcggtgctc gcgcccctcg gtggcgaaca     360
gcagccgctt gcgatccagg tcgtgcacga cggtgatgta gtgctgcccg cgccgcaggc     420
tggtctcgtc gatgcccacc gtgcgcacgc cggcgaagtc ttccagcgca cgcgcctgcg     480
cgacgtagaa ctcgatgcgc cgccacagcc gcttgtcctt gcagcgcagc aactcggcgg     540
cctggcgcac cggcaggtcc aggcacaagg tcagcgccag cgcttcgaac gccgcggtga     600
agcccgagcc cggacgcgcc cagggcacgg ccacctgcgt ggtcttgccg caggcaccgc     660
aggccacgcg cggcacgtcg cagtgcagcc aggcctcgaa ctggaagaag tccaggtgcc     720
gccaggatcg gcgcagccgg tcgtgcaccg gttgcgtggc cgcaccgcat gccgggcagg     780
cgagcctgct ggtgtggcag ccgatctcga agtcgatacg ccgcttggcc gtgtcgagcc     840
tgacgtcatc gacgacccac ggcggctgca agcccagcgc gctggtgaac agagcttcta     900
cggcaatgcc catggctcat cctcctgatc aaacacgcct cgtggacatg tgcacaggcc     960
ggccagcggc ctgcacacat gcccaccggg ctcgacgacc aggagtcatt gtgactgttg    1020
ggttccacac gaaatgacga aggaccccta gtgtgcgggg ttatcgtacc ggtgagaacc    1080
cgacacgatg gcaaggtttt gaccaacatg ctaaaaggcc cattcaaacc aactaccccg    1140
gagccagcca tgccacgatc cctactcacc gacgctgacg tgcgttcggt cagcgattcc    1200
gtcgccctcg gcctgccgtc cgaacgcatg gcgtcccttg ccgaggcgtt caacctgatg    1260
gtgctgccga ccctccagca actcgatgcg gtcaatccg gtgaaatcca gccggcacct    1320
gccttcgacc cgcgctggaa ggaggtgcag tcatgagttc gctaacccgc ctcaccctcg    1380
```

-continued

```
cgcaagttgc gcagaaactt aaggcacggg aagtctccgc cgttgaagtt ctggacgcct    1440
gtctgacgca ggtgcgctcc accgaaaaac agatcagtgc gtacgtgtgc gtgctggagg    1500
atcaggcccg tgcagcagcc cagcaagctg acgccgacat cagcgccggg cgctggaaag    1560
gcccgctgca tggcgtgcct gtagcggtca aggacttata cgacatcgct ggcgtaccca    1620
ccacggcatc gtcgcgccag cgcacgaatt ggacgccgca gcaagactgc gccgtagtcc    1680
ggcgcttgaa agacgcaggt gccgttatcc ttggcaagac ccatacgcac gaattcgcct    1740
atggcgtcat cactccgaag tcgcgcaacc cctgggaccc gggaagaaca ccgggtggct    1800
ccagcggcgg ctcggcggcc acggtcgcag cctgcggcgt ctacttggcg accggcaccg    1860
acaccggtgg atccgttcgc atcccttcgt cgatgtgcaa caccgtaggc ctgaagccaa    1920
cctacgggcg cgtgagccgt gccggtgtga gttcactttc ctggagcctg gaccatccag    1980
gcccgatcac gcgcaccgtg gaagacacgc gctcagcct tcaggtgatg gctggcttcg    2040
atccagccga ccgcggctcg ttggatgagc cggtgcccag ctatgccgaa gggctcggcc    2100
aaggcgtgaa aggcctgcgc gtgggcgtgc cgaagaacta cttcttcgac cgcgtggacc    2160
cggaagttga aagtgcggtt cgtgccgcca tcgatcaact gaaagagctg ggcgccgaac    2220
tggtggaagt cgaagtgccc atggccgagc agatcatccc ggtggagttc gggatcgtgc    2280
tacccgaagc cagcgcctac caccgcacga tgctgcgcga gtcacccgag ctctacaccg    2340
ccgatgtccg catactgctg gaactcggaa atctagtcac cgccaccgac tacctgcagg    2400
cgcagcgcgt ccgtacgctg atgcagcgcg cggtggccga gatgttccag cgcatcgatg    2460
tgctgatcgc acccacactg cccatcccgg ctgctcgcag cggggaggag gtccacacat    2520
ggccggacgg cacggtagag gcgttgttca tggcctatac gcgcttcacc tcgttcggca    2580
acgtgacagg attacccacg ctgaacctgc cctgtggttt ctccaaggat gggttgccga    2640
tcggcatgca gatcaccggc cggccgctgg acgagaagac cctgctgcgt gctgggctgg    2700
cctacgagaa agccacgacc tggcaccagc gtcatccgga actgatcgga gcgggctgag    2760
ctgcaagaaa gcaggcgcgg cggcgcacga cccattgtgc taccgctgcg tctgcctgaa    2820
gtggccgaga ccaagcagaa gaaggaggtg acatagcctc ctacaatctg ccgtcttctc    2880
ggagccctct ggatgctcga agttctttgc atggggttgc gccgggagcg caatctgcaa    2940
ggtggcattg gccttcagtg tcgatgccga gttgaagtcg ctgtaccccct tttttcaacc    3000 acaccaggag aaccgcacca tggggcaatc acacacgcat gaccaccatc acgacgggta    3060
ccaggcaccg cccgaagaca tcgcgctgcg ggtcaaggcc ttggagtctc tgctgatcga    3120
gaaaggtctt gtcgacccag cggccatgga cttggtcgtc caaacgtatg aacacaaggt    3180
aggcccccga aacggcgcca aagtcgtggc caaggcctgg gtggaccctg cctacaaggc    3240
ccgtctgctg gcagacggca ctgccggcat tgccgagctg gcttctccg gggtacaggg    3300 cgaggacatg gtcattctgg aaaacacccc cgccgtccac aacgtcgtcg tttgcacctt    3360
gtgctcttgc tacccatggc cgacgctggg cttgcccct gcctggtaca aggccccgcc    3420
ctaccggtcc cgcatggtga cgacccgcg tggggttctc gcggagttcg gcctggtgat    3480
ccccgcgaag gaaatccgcg tctgggacac cacggccgaa ttgcgctaca tggtgctgcc    3540
ggaacggccc gcgggaactg aagcctacag cgaagaacaa ctggccgaac tcgttacccg    3600
cgattcgatg atcggcaccg gcctgcccat ccaacccacc ccatctcatt aaggagttcg    3660
tcatgaatgg cattcacgat actggggggag cacatggtta tgggccggtt tacagagaac    3720
```

```
cgaacgaacc cgtctttcgc tacgactggg aaaaaacggt catgtccctg ttcccgcgc    3780
tgttcgccaa cggcaacttc aacctcgatg agtttcgaca cggcatcgag cgcatgaacc    3840
ccatcgacta cctgaaggga acctactacg aacactggat ccattccatc gaaaccttgc    3900
tggtcgaaaa gggtgtgctc acggcaacgg aactcgcgac cggcaaggca tctggcaaga    3960
cagcgacacc ggtgctgacg ccggccatcg tggacggact gctcagcacc ggggcttctg    4020
ccgcccggga ggagggtgcg cgggcgcggt tcgctgtggg ggacaaggtt cgcgtcctca    4080
acaagaaccc ggtgggccat acccgcatgc cgcgctacac gcggggcaaa gtggggacag    4140
tggtcatcga ccatggtgtg ttcgtgacgc cggacaccgc ggcacacgga aagggcgagc    4200
accccccagca cgtttacacc gtgagtttca cgtcggtcga actgtggggg caagacgcct    4260
cctcgccgaa ggacacgatt cgcgtcgact tgtgggatga ctacctggag ccagcgtgat    4320
catgaaagac gaacggtttc cattgccaga gggttcgctg aaggacctcg atggccctgt    4380
gtttgacgag ccttggcagt cccaggcgtt tgccttggtg gtcagcatgc acaaggccgg    4440
tctctttcag tggaaagact gggccgagac cttcaccgcc gaaatcgacg cttccccggc    4500
tctgccggc gaaagcgtca acgacaccta ctaccggcaa tgggtgtcgg cgctggaaaa    4560
gttggtggcg tcgctggggc ttgtgacggg tggagacgtc aactcgcgcg cacaggagtg    4620
gaaacaggcc cacctcaaca ccccacatgg gcacccgatc ctgctggccc atgcgctttg    4680
cccgccagcg atcgacccca agcacaagca cgagccaaaa cgctcaccga tcaaggtcgt    4740
tgccgcaatg gcttgagatc cactgtcctg tttccctacc ttgaatggag taaaccatga    4800
gttcattttc taccactgcc gtccccgccg cccagcgcct gagcgccacg cgcagcttac    4860
tgttgcaact gtccgctggc gccgcgctgg gcctggtcgt cctgtacggc gtggcttttg    4920
ccgaaagccc gcttgcgcac aacgccgcgc acgatgttcg ccacgtgacg gtcaagcctt    4980
gtcactaact gtggcccacc ccgccgcgc tgcgcgcgac cccctccagg ggcaaaccg    5040
agtggcccgg cggagccggt tccaccgcgt tcccggtggg gtgcactgct ggcgttgcgg    5100
gtcttgtttc ggctggatgg tttcttgacg gagccacacc gtcgctcatc tgtatatgga    5160
gagggtcatg atttttcgac gcttgatctg ggcggcgctg gccgtggcct tgctggtggg    5220
cagtttgcag tcgggtctgc agcagttgca gaccgtgccc atcatcctgg cggccgaggt    5280
gtttgagggc cagaaggtgg ccgcgcccga gccggtggca acaccggccg gtgcggctgc    5340
gcacgtccat gcggacggtg cgacacacga ccatggcgac gccgccgaag cctgggcgcc    5400
cgccgacggg gtggagcgcc acttctggac ctgggtggcc aatgtgctgc acgcgttcag    5460
catggcgctg ctggtgctgg ccgtgatggc ggtgtgccag tggcgcggca gcgccttgcg    5520
cgctgtgcct ttggccgcct gggtggccgc cgccggttgg ctgagcttc acttctggcc    5580
ttcgctgggc ctgcacgccg agatccccgg catggatgcc gcccggctgg gttcacgcca    5640
gggctggtgg gtgctcgcgg cgggcggtgc ggcgctggcc tgtgcgtcgg tggcgctgat    5700
gcgcagcccc ctgcgctggg ccgctgcaat ggcttgtctg gcgctgccct tcgtggtggg    5760
cgcgccgcac atcgtggccg acccgctggc cggtttcacg ggtgaggctc aggcggcgct    5820
gcgtgaactg ggccgccagt tcatctgggc caccacctgg ttgtcgctgt cgttctgggt    5880
gagtatgggc gtggtggccg gtctggcctt ccagcgctgg ctgagcccg ccgtggcggc    5940
gctgctgcag cgcacggaca ccgcccgggc cccagccatg gagacgccgc gataagcgac    6000
gtcaacgcaa gggtcgtgcg gggtgctgat ctgaaccgcc tttttttttg aggaggctct    6060
tttccctgag aggatagagc catgagcaag aagtcgaacc agttttcacc cgaagtgcgc    6120
```

```
gagcgtgctg ttcgcatggt gctggagcac cgaggcgagt acccatctct gtgggccgcc    6180
atcgattcga tcgcgcccaa gatcggttgt gtgccgcaga ccctgcatac ctgggtcaag    6240
cgtgtcgagg tcgacagcgg cgtgcgtgag ggcgtcagca cttccgagct gcagcgtctg    6300
aaggagctcg aacgcgagaa caaggagctg cgcaaggcca acgagatctt gaagctggcc    6360
agcgcgtttt tcgcccaggc ggagctcgac cgccgtctga agcccgaag ggcttcatcg    6420 accagtatcg acaggcctac ggggtcgagt cgatctgcaa ggtgttgcag gtcgccccgt    6480
caggctattg cgccacgcc gctcaacaac gcaaccccca actgcgctgt ccgtgcgctc    6540
aacgtgacga cccctggtg gcgcacattg aacgcgtctg gcaggccaac atgcgggtct    6600
atggcgccga caaggtctgg aagcaaatga accgcgaggg cattgtggtg gcgcgctgca    6660
cggtcgagcg gctgatgcgg cgcctgcgct tgcagggcgt gcgccgtggc aaggtggtgc    6720
gtaccaccat cagcgatggt cgggcgccgt gcccgctgga ccgggtcaac cgggtgttca    6780
gagcagaccg gcccaaccag ctctgggtct cggacttcac ctacgtgtcg acctggcagg    6840
gctggctgta cgtggccttc gtgatcgatg tgtacgcccg gcgcatcgtg ggctggcggg    6900
taagcagttc gatgcgcacg gacttcgtgc tcgatgccct ggaacaggcg ctgtatgcgc    6960
gccagcctga gcgcgatggc agcctggttt gccactccga cagggggtcg caatacgtca    7020
gcatccgcta caccgagcga ctggcccagg ccggtatcga gccctcggtg ggcagcaaag    7080
gtgacagcta cgacaacgcg ctggccgaga cgatcaacgg gctgtacaag gccgaattga    7140
tccatcggcg agccccatgg aggaccaagg agtcggtgga gctggctacc ctcccatggg    7200
tgtcatggtt caaccaccac cggctgctcg aacccatcgg ctacatcccg ccggccgagg    7260
ctgaggcaaa ctactaccgg caactcgcca atcaggcctc catggtggtg gcctgactta    7320
aaccaaccgg cctccacgat tcccggggcg gttcaagagc ctcctatttc ctgtccaata    7380
ggagcccgta tgagcagtca acgttacccg aattc                              7415
```

<210> SEQ ID NO 19
<211> LENGTH: 31
<212> TYPE: DNA
<213> ORGANISM: artificial sequence
<220> FEATURE:
<223> OTHER INFORMATION: Primer 4

<400> SEQUENCE: 19
ttatctagac ccgcgctgga aggaggtgca g                                   31

<210> SEQ ID NO 20
<211> LENGTH: 29
<212> TYPE: DNA
<213> ORGANISM: artificial sequence
<220> FEATURE:
<223> OTHER INFORMATION: Primer 5

<400> SEQUENCE: 20
cagaagcttt cttgcagctc agcccgctc                                      29

<210> SEQ ID NO 21
<211> LENGTH: 33
<212> TYPE: DNA
<213> ORGANISM: artificial sequence
<220> FEATURE:
<223> OTHER INFORMATION: Primer 6

<400> SEQUENCE: 21

```
tatgaattca tgagttcgct aacccgcctc acc                              33
```

<210> SEQ ID NO 22
<211> LENGTH: 40
<212> TYPE: DNA
<213> ORGANISM: artificial sequence
<220> FEATURE:
<223> OTHER INFORMATION: Primer 7

<400> SEQUENCE: 22

```
tagcggccgc ttagcccgct ccgatcagtt ccggatgacg                        40
```

<210> SEQ ID NO 23
<211> LENGTH: 3449
<212> TYPE: DNA
<213> ORGANISM: Comamonas testosteroni 5-MGAM-4D

<400> SEQUENCE: 23

```
tatgaattca tgagttcgct aacccgcctc accctcgcgc aagttgcgca gaaacttaag    60
gcacgggaag tctccgccgt tgaagttctg gacgcctgtc tgacgcaggt gcgctccacc   120
gaaaaacaga tcagtgcgta cgtgtgcgtg ctggaggatc aggcccgtgc agcagcccag   180
caagctgacg ccgacatcag cgccgggcgc tggaaaggcc cgctgcatgg cgtgcctgta   240
gcggtcaagg acttatacga catcgctggc gtacccacca cggcatcgtc gcgccagcgc   300
acgaattgga cgccgcagca agactgcgcc gtagtccggc gcttgaaaga cgcaggtgcc   360
gttatccttg gcaagaccca tacgcacgaa ttcgcctatg gcgtcatcac tccgaagtcg   420
cgcaacccct gggacccggg aagaacaccg ggtggctcca gcggcggctc ggcggccacg   480
gtcgcagcct gcggcgtcta cttggcgacc ggcaccgaca ccggtggatc cgttcgcatc   540
ccttcgtcga tgtgcaacac cgtaggcctg aagccaacct acgggcgcgt gagccgtgcc   600
ggtgtgagtt cactttcctg gagcctggac catccaggcc cgatcacgcg caccgtggaa   660
gacacggcgc tcagccttca ggtgatggct ggcttcgatc cagccgaccg cggctcgttg   720
gatgagccgg tgcccagcta tgccgaaggg ctcggccaag gcgtgaaagg cctgcgcgtg   780
ggcgtgccga gaactactt cttcgaccgc gtggacccgg aagttgaaag tgcggttcgt   840
gccgccatcg atcaactgaa agagctgggc gccgaactgg tggaagtcga agtgcccatg   900
gccgagcaga tcatcccggt ggagttcggg atcgtgctac ccgaagccag cgcctaccac   960
cgcacgatgc tgcgcgagtc acccgagctc tacaccgccg atgtccgcat actgctggaa  1020
ctcggaaatc tagtcaccgc caccgactac ctgcaggcgc agcgcgtccg tacgctgatg  1080
cagcgcgcgg tggccgagat gttccagcgc atcgatgtgc tgatcgcacc cacactgccc  1140
atcccggctg ctcgcagcgg ggaggaggtc cacacatggc cggacggcac ggtagaggcg  1200
ttgttcatgg cctatacgcg cttcacctcg ttcggcaacg tgacaggatt acccacgctg  1260
aacctgccct gtggtttctc caaggatggg ttgccgatcg gcatgcagat caccggccgg  1320
ccgctggacg agaagaccct gctgcgtgct gggctggcct acgagaaagc cacgacctgg  1380
caccagcgtc atccggaact gatcggacgc ggctgagctg caagaaagca ggcgcggcg  1440 cgcacgaccc attgtgctac cgctgcgtct gcctgaagtg gccgagacca agcagaagaa  1500
ggaggtgaca tagcctccta caatctgccg tcttctcgga gccctctgga tgctcgaagt  1560
```

```
tctttgcatg gggttgcgcc gggagcgcaa tctgcaaggt ggcattggcc ttcagtgtcg   1620
atgccgagtt gaagtcgctg taccccttt ttcaaccaca ccaggagaac cgcaccatgg   1680
ggcaatcaca cacgcatgac caccatcacg acgggtacca ggcaccgccc gaagacatcg   1740
cgctgcgggt caaggccttg gagtctctgc tgatcgagaa aggtcttgtc gacccagcgg   1800
ccatggactt ggtcgtccaa acgtatgaac acaaggtagg cccccgaaac ggcgccaaag   1860
tcgtggccaa ggcctgggtg gaccctgcct acaaggcccg tctgctggca gacggcactg   1920
ccggcattgc cgagctgggc ttctccgggg tacagggcga ggacatggtc attctggaaa   1980
acaccccgc cgtccacaac gtcgtcgttt gcaccttgtg ctcttgctac ccatggccga   2040
cgctgggctt gccccctgcc tggtacaagg ccccgcccta ccgtcccgc atggtgagcg   2100
acccgcgtgg ggttctcgcg gagttcggcc tggtgatccc cgcgaaggaa atccgcgtct   2160
gggacaccac ggccgaattg cgctacatgg tgctgccgga acggcccgcg ggaactgaag   2220
cctacagcga agaacaactg gccgaactcg ttacccgcga ttcgatgatc ggcaccggcc   2280
tgcccatcca acccaccca tctcattaag gagttcgtca tgaatggcat tcacgatact   2340
gggggagcac atggttatgg gccggtttac agagaaccga acgaacccgt ctttcgctac   2400
gactgggaaa aaacggtcat gtccctgttc ccggcgctgt tcgccaacgg caacttcaac   2460
ctcgatgagt ttcgacacgg catcgagcgc atgaacccca tcgactacct gaagggaacc   2520
tactacgaac actggatcca ttccatcgaa accttgctgg tcgaaaaggg tgtgctcacg   2580
gcaacggaac tcgcgaccgg caaggcatct ggcaagacag cgacaccggt gctgacgccg   2640
gccatcgtgg acggactgct cagcaccggg gcttctgccg cccggaggga gggtgcgcgg   2700
gcgcggttcg ctgtgggga caaggttcgc gtcctcaaca agaacccggt gggccatacc   2760
cgcatgccgc gctacacgcg gggcaaagtg gggacagtgg tcatcgacca tggtgtgttc   2820
gtgacgccgg acaccgcggc acacggaaag ggcgagcacc cccagcacgt ttacaccgtg   2880
agtttcacgt cggtcgaact gtgggggcaa gacgcctcct cgccgaagga cacgattcgc   2940
gtcgacttgt gggatgacta cctggagcca gcgtgatcat gaaagacgaa cggtttccat   3000
tgccagaggg ttcgctgaag gacctcgatg gccctgtgtt tgacgagcct tggcagtccc   3060
aggcgtttgc cttggtggtc agcatgcaca aggccggtct ctttcagtgg aaagactggg   3120
ccgagacctt caccgccgaa atcgacgctt ccccggctct gcccggcgaa agcgtcaacg   3180
acacctacta ccggcaatgg gtgtcggcgc tggaaaagtt ggtggcgtcg ctggggcttg   3240
tgacgggtgg agacgtcaac tcgcgcgcac aggagtggaa acaggcccac ctcaacaccc   3300
cacatgggca cccgatcctg ctggcccatg cgctttgccc gccagcgatc gaccccaagc   3360
acaagcacga gccaaaacgc tcaccgatca aggtcgttgc cgcaatggct tgagatccac   3420
tgtcctgttt ccctaccttg aagcttcag                                    3449
```